(12) United States Patent
Priscal et al.

(10) Patent No.: US 11,939,132 B2
(45) Date of Patent: Mar. 26, 2024

(54) PRODUCT PACKAGING WITH HEAT SEALABLE BARRIER MATERIAL

(71) Applicant: AMCOR FLEXIBLES NORTH AMERICA, INC., Neenah, WI (US)

(72) Inventors: Michael D. Priscal, Neenah, WI (US); Kevin P. Nelson, Appleton, WI (US)

(73) Assignee: AMCOR FLEXIBLES NORTH AMERICA, INC., Neenah, WI (US)

( * ) Notice: Subject to any disclaimer, the term of this patent is extended or adjusted under 35 U.S.C. 154(b) by 483 days.

(21) Appl. No.: 17/295,784

(22) PCT Filed: Dec. 31, 2018

(86) PCT No.: PCT/US2018/068146
§ 371 (c)(1),
(2) Date: May 20, 2021

(87) PCT Pub. No.: WO2020/142068
PCT Pub. Date: Jul. 9, 2020

(65) Prior Publication Data
US 2022/0024663 A1  Jan. 27, 2022

(51) Int. Cl.
*B65D 75/36* (2006.01)
*A61J 1/03* (2023.01)
(Continued)

(52) U.S. Cl.
CPC ............. *B65D 75/36* (2013.01); *A61J 1/035* (2013.01); *A61J 1/10* (2013.01); *A61K 31/352* (2013.01);
(Continued)

(58) Field of Classification Search
CPC .. B65D 75/36; A61J 1/035; A61J 1/10; A61K 31/352; A61K 31/4468; A61K 31/465;
(Continued)

(56) References Cited

U.S. PATENT DOCUMENTS 4,701,360 A    10/1987  Gibbons et al.
4,977,004 A    12/1990  Bettle, III et al.
(Continued)

FOREIGN PATENT DOCUMENTS

WO        0200430 A2     1/2002
WO     2017114922 A1     7/2017

OTHER PUBLICATIONS

PCT International Search report, international application No. PCT/US2018/068146, dated Mar. 25, 2019, 2 pgs.
(Continued)

*Primary Examiner* — James C Yager

(57) ABSTRACT

A package that is suitable for packaging an article for collecting or administering a pharmaceutical active substance is disclosed. The package includes a first packaging component that includes a product-contacting sealant layer that includes a first ethylene vinyl alcohol copolymer. The package includes a second packaging component that includes a product-contacting sealant layer that includes a second ethylene vinyl alcohol copolymer. The ethylene content of the second ethylene vinyl alcohol copolymer is equal to or less than about 38 percent and the ethylene content of the first ethylene vinyl alcohol copolymer is greater than the ethylene content of the second ethylene vinyl alcohol copolymer.

18 Claims, 9 Drawing Sheets

(51) Int. Cl.
*A61J 1/10* (2006.01)
*A61K 31/352* (2006.01)
*A61K 31/4468* (2006.01)
*A61K 31/465* (2006.01)
*B29C 65/00* (2006.01)
*B29C 65/02* (2006.01)
*B32B 27/08* (2006.01)
*B32B 27/30* (2006.01)
*B29K 23/00* (2006.01)

(52) U.S. Cl.
CPC ........ *A61K 31/4468* (2013.01); *A61K 31/465* (2013.01); *B29C 65/02* (2013.01); *B29C 66/72321* (2013.01); *B29C 66/72341* (2013.01); *B29C 66/72343* (2013.01); *B32B 27/08* (2013.01); *B32B 27/306* (2013.01); *B29K 2023/083* (2013.01); *B29K 2023/086* (2013.01); *B29K 2995/0067* (2013.01); *B29K 2995/0069* (2013.01); *B32B 2307/7244* (2013.01); *B32B 2307/7246* (2013.01); *Y10T 428/1379* (2015.01)

(58) Field of Classification Search
CPC .................. A61K 9/7084; B29C 65/02; B29C 66/72321; B29C 66/72341; B29C 66/72343; B29C 65/08; B29C 65/38; B29C 65/8223; B29C 66/112; B29C 66/131; B29C 66/24244; B29C 66/53461; B29C 66/71; B29C 66/712; B32B 27/08; B32B 27/306; B32B 2307/7244; B32B 2307/7246; B32B 2250/05; B32B 7/02; B32B 15/082; B32B 15/20; B32B 27/10; B32B 27/304; B32B 27/36; B32B 2255/20; B32B 2255/205; B32B 2270/00; B32B 2307/31; B32B 2307/738; B32B 2435/02; B32B 2439/80; B32B 27/18; B32B 27/302; B32B 27/32; B32B 27/34; B32B 2307/406; B32B 2307/732; B32B 27/308; B32B 2255/10; B32B 2307/748; B32B 2439/06; B32B 2439/46; B32B 7/12; B32B 1/00; B29K 2023/083; B29K 2023/086; B29K 2995/0067; B29K 2995/0069; B29K 2023/065; B29K 2027/06; B29K 2023/38; Y10T 428/1379; B29L 2031/7164

See application file for complete search history.

(56) References Cited

U.S. PATENT DOCUMENTS

| | | |
|---|---|---|
| 2002/0071923 A1 | 6/2002 | Cullision et al. |
| 2003/0087115 A1 | 5/2003 | Ferri |
| 2011/0027428 A1 | 2/2011 | Bekele |
| 2012/0000166 A1 | 1/2012 | Mueller et al. |
| 2017/0029156 A1 | 2/2017 | Eguchi et al. |
| 2017/0158400 A1 | 6/2017 | Priscal et al. |
| 2018/0281365 A1 | 10/2018 | Moffitt |

OTHER PUBLICATIONS

EVAL Europe NV, "EVAL™ EVOH Resins", https://www.kuraray.eu/fileadmin/presse/publikationen/downloads_k_fair_2013/eval/EVAL_Technical_Brochure_English_version.pdf, pp. 1-28, Apr. 2011.
EVAL, "Medical and pharmaceutical", http://www.evalevoh.com/media/125446/eval_and_kurarister_for_medical_and_pharma_emea_.pdf, pp. 1-8.
Kiang, Webster W., Ph.D., "Hot Tack and Heat Sealing Properties of EVOH", TAPPI Proceedings, Polymers, Laminations & Coatings Conference, 1992, pp. 335-358.

PRODUCT PACKAGING WITH HEAT SEALABLE BARRIER MATERIAL

TECHNICAL FIELD

The present disclosure relates generally to packages suitable for packaging an article for collecting or administering a physiologically active substance such as blister packaging for a capsule product or a pouch for a transdermal patch product where the product includes a pharmaceutical active agent.

BACKGROUND

Blister packaging is employed widely for commercial packaging of food products, personal care products, and human health products such as pharmaceuticals, medical devices or precision instruments. The use of this type of packaging has become widespread mainly due to the ability to incorporate suitable moisture, dust, UV and/or gas barriers into the packages when such properties are desired for maintaining the product contained therein. For example, blister packaging is extensively used in the pharmaceutical industry for packaging of medicaments, pharmaceutical active agents or the like, for example, in the form of 1) capsules, lozenges, or pills, or 2) cartridges, vials or containers that may contain the pharmaceutical active agent. The integrity of the pharmaceutical active agent can be maintained through the proper selection of materials used to form the packages.

Further, pharmaceuticals such as the drugs fentanyl and nicotine are often administered through the use of transdermal patches which are applied to a patient's skin to permit drug delivery over time by absorption. Prior to application of a drug containing patch, the patch is packaged in a pouch which is designed to be opened to permit access to the patch by the patient or caregiver for application to a patient's skin. Suitable packaging for transdermal patches should contain the patch and its drug within the package while protecting the patch from contamination and deleterious effects from the external environment. Thus, packaging in the form of a pouch may hold a transdermal patch to protect the patch and its drug contents from contact or exposure to unwanted materials such as microbes, insects, air, moisture, sunlight, etc. The packaging is typically sealed, for example, by a heat seal to provide a hermetic barrier.

The materials used in constructing packages for containing pharmaceutical active agents, especially the product-contacting interior surface layer of the package, should resist migration of chemicals between the product and the package materials. Such migration of the active agents from the product to the package structure is referred to as "scalping". In the case of commercial transdermal patches, some patches include levels of chemicals or drugs that are several times higher than the intended, released dose to mitigate the effect of scalping. For example, a commercial, transdermal nicotine patch that can release a dose of 21 mg of nicotine may contain several times more nicotine such as, for example, 100 mg, 110 mg, 120 mg, 130 mg, 140 mg, or even 150 mg of nicotine. A common material employed for the product-contacting package interior surface layer that prevents scalping is polyacrylonitrile, which is often sold under the BAREX trademark by Ineos AG. Another common material that prevents scalping is cyclic olefin copolymer (COC), which is often sold under the TOPAS trademark by TOPAS Advanced Polymers GmbH. While these materials have superb anti-scalping properties, they have limited availability which creates supply chain risk. Other polymers used in the product-contacting package interior surface layers include polyester (e.g. polyethylene terephthalate (PET)). PET suffers from the disadvantage of being less resistant to scalping of certain chemicals than desired.

Packaging for pharmaceuticals or other moisture-sensitive articles require not only low moisture permeability but also other properties such as chemical inertness, clarity, rigidity, or uniform thickness. Some moisture barriers include polymers formed from halogenated molecules such as polyvinylidene chloride (PVdC) and polychlorotrifluoroethylene (PCTFE), which is commonly referred to as ACLAR (available from Honeywell International Corporation). However, while ACLAR exhibits relatively low moisture vapor transmission, its use in blister packaging is inherently costly and it is difficult to heat seal.

The packaging includes polymers that provide limits to or slows the ingress of oxygen. Packaging that includes an oxygen barrier can prevent premature degradation of products susceptible to oxidation that are contained within the packaging. Some oxygen barriers include polymers formed from halogenated molecules such as PVdC. Although packaging that incorporate these resins provide effective barriers, they may contribute towards undesired effects. For example, fluoropolymers, while being relatively chemically inert, may not serve as effective seal layers.

Accordingly, there is a need to provide improved packaging that addresses the aforementioned concerns.

SUMMARY

The disclosure relates to packaging for products that contain a pharmaceutical active agent. The packaging includes anti-scalping product-contacting layers that resist the migration of chemicals. Additionally, the packaging includes product-contacting layer materials that are heat sealable and may be capable of forming hermetic seals. Further the product-contacting sealant layer materials are readily available and provide barrier properties to the package.

In one embodiment, package includes a first packaging component that includes a product-contacting sealant layer that includes a first ethylene vinyl alcohol copolymer. The package includes a second packaging component that includes a product-contacting sealant layer that includes a second ethylene vinyl alcohol copolymer. The ethylene content of the second ethylene vinyl alcohol copolymer is equal to or less than about 38 percent. The ethylene content of the first ethylene vinyl alcohol copolymer is greater than the ethylene content of the second ethylene vinyl alcohol copolymer.

Other features that may be used individually or in combination with respect to the above-mentioned embodiment or any embodiment of the present application are as follows.

The ethylene content of the second ethylene vinyl alcohol copolymer is 38 percent.

The ethylene content of the first ethylene vinyl alcohol copolymer is greater than 38 percent.

The first packaging component comprises at least 95 wt. percent of the first ethylene vinyl alcohol copolymer and the second packaging component comprises at least 95 wt. percent of the second ethylene vinyl alcohol copolymer.

The first packaging component consists essentially of the first ethylene vinyl alcohol copolymer and the second packaging component consists essentially of the second ethylene vinyl alcohol copolymer.

The first and second ethylene vinyl alcohol copolymers are heat sealed to each other under conditions of 163 degrees Celsius to 193 degrees Celsius, 1 second dwell time and 0.2 MPa pressure. The peak heat seal strength is at least 525 Newton/m (3 pounds-force/inch) when tested according to ASTM F88.

The package includes a water or moisture transmission rate (WVTR) 0.1 g/m2/24 hours at 38 degrees Celsius and 90 percent relative humidity according to ASTM F1249.

The package includes an oxygen transmission rate (OTR) of equal to or less than 0.25 cc/m2/24 hours at 1 atmosphere and 23 degrees Celsius and 0 percent relative humidity according to ASTM F1927.

The package is in the form of a pouch, sachet, or thermoformed blister and/or tray and lid.

The package further includes a pharmaceutical active agent that is hermetically sealed within the package. The pharmaceutical active agent is selected from the group consisting of nicotine, tetrahydrocannabinol (THC), fentanyl, acetylfentanyl, lidocaine, clonidine, ethinyl estradiol, estradiol, oxybutynin, buprenorphine, granisetron, methylphenidate, and scopolamine.

The package further includes a RED value of 1.0 or greater.

In another embodiment, a package includes a first packaging component that includes a first ethylene vinyl alcohol copolymer. The package includes a second packaging component that includes a second ethylene vinyl alcohol copolymer. The first ethylene vinyl alcohol copolymer has an ethylene content of about 48 mol percent. The second ethylene vinyl alcohol copolymer has an ethylene content of about 38 mol percent. The first and second ethylene vinyl alcohol copolymers are heat sealed to each other.

Other features that may be used individually or in combination with respect to this embodiment are as follows.

The first packaging component is a flexible film and the second packaging component is a formable film.

A packaged product is located between the first packaging component and the second packaging component of the package. The product comprises a pharmaceutical active agent. The pharmaceutical active agent includes nicotine, tetrahydrocannabinol (THC), acetylfentanyl, lidocaine, or a combination thereof.

In a further embodiment, a package includes a first packaging component that includes a product-contacting sealant layer that includes a first ethylene vinyl alcohol copolymer and an aluminum foil layer. The package includes a second packaging component that includes a product-contacting sealant layer that includes a second ethylene vinyl alcohol copolymer and a barrier layer that includes ethylene vinyl acetate (EVA). The first ethylene vinyl alcohol copolymer has an ethylene content of about 48 mol percent. The second ethylene vinyl alcohol copolymer has an ethylene content of about 38 mol percent. The first and second ethylene vinyl alcohol copolymers are heat sealed to each other.

BRIEF DESCRIPTION OF THE DRAWINGS

Other objects and advantages of the present disclosure will become more apparent to those skilled in the art in view of the following description and the accompanying figures.

Figure 1:
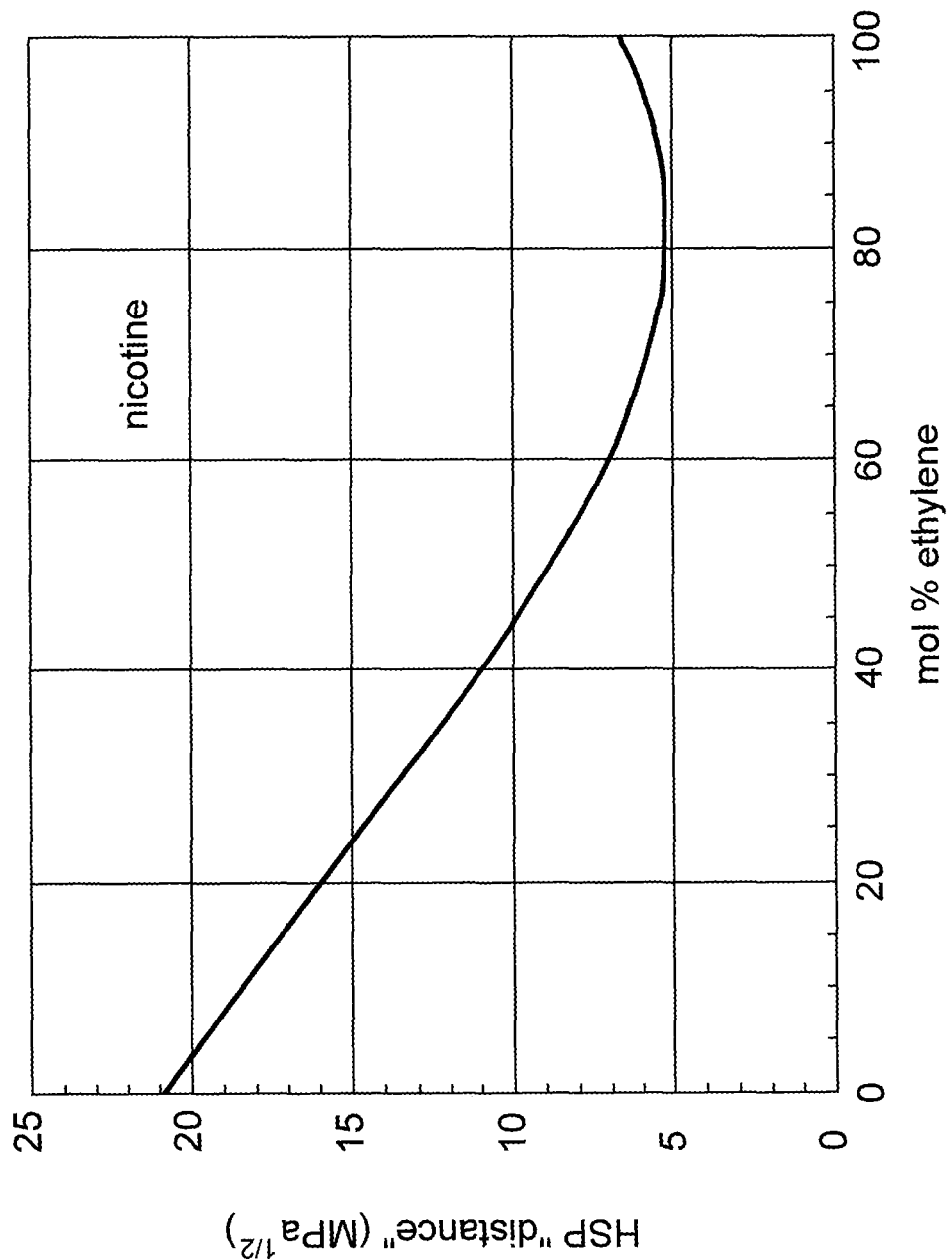
FIG. 1 illustrates a graphical representation of the Hansen Solubility Parameter distance for EVOH at varying ethylene contents against nicotine solubility.

The figures show some but not all embodiments. The figures are not necessarily to scale. Like numbers used in the figures refer to like components. It will be understood, however, that the use of a number to refer to a component in a given figure is not intended to limit the component in another figure labeled with the same number.

DETAILED DESCRIPTION

The present disclosure relates to, among other things, packaging for products that contain a pharmaceutical active agent product. The packages include packaging components that each include a sealant layer. The sealant layers resist migration of chemicals, such as pharmacological active agents or excipients, between the product and the sealant layers of the package. Thus, each sealant layer is an anti-scalping layer. In a packaged product, the anti-scalping sealant layer can be in contact with the pharmaceutical active agent. As used herein, "in contact with the pharmaceutical active agent," in the context of a layer of a film, means that under typical storage conditions some portion of the active agent will contact the layer. The active agent may be in direct contact with the sealant layer or may be in indirect contact with the layer. Indirect contact between the active agent and the sealant layer can occur, for example, due to volatilization of the active agent or an active agent carrier within the package to cause the active agent, which is not stored in direct contact with the sealant layer, to contact the layer. However, even if the active agent is not in contact with the sealant layer, it may be desirable for the sealant layer to be anti-scalping to provide assurance that if an active agent accidentally became exposed to the sealant layer, the sealant layer would not substantially scalp the active agent. Thus, the sealant layer, as used herein, may be referred to as "a product-contacting layer" or "product-contacting sealant layer".

The term "film", as used herein refers to a polymeric web of any thickness. The polymeric web may be flexible, semi-rigid or rigid.

The term "layer", as used herein, refers to a structure of a single polymer-type or a blend of polymers that may be accompanied by additives and that may be continuous or discontinuous.

The terms "seal layer", "sealing layer", "heat seal layer", and "sealant layer", as used herein, refer to a film layer, or layers, involved in the sealing of the film: to itself, to another film layer of the same film or another film, and/or to another article which is not a film, for example, a tray. In general, the sealant layer is a surface layer, that is, an exterior or an interior layer of any suitable thickness, that provides for the sealing of the film to itself or another layer. With respect to packages having only fin-type seals, as opposed to lap-type seals, the phrase "sealant layer" generally refers to the interior surface film layer of a package. The inside layer frequently can also serve as a product-contacting layer in the packaging of products.

Packaging Components

The packages of the present disclosure include a first packaging component and a second packaging component. The first and second packaging components may each be a flexible polymeric film or a formable polymeric film, for example, that can be thermoformed to some degree. The first and second packaging components may each include non-polymeric components. The first and second packaging components each include a sealant layer and are configured such that the sealant layers may be product-contacting sealant layers. The first and the second packaging components are sealed to each other via the sealant layers of each packaging component to form a package forming an enclosure wherein a product may be contained within. The package may be, for example, a pouch or a sachet, such that the first and second packaging components are each flexible. The package may be, for example, 1) in a rigid form where each the first and second packaging components are rigid (to some extent), or 2) in a form where one of the first or second packaging components is rigid and the other of the first or second flexible packaging components is flexible. For example, the package may be in the form of a thermoformed blister and a lid, a thermoformed tray and a lid, a tray and a lid, a container and a lid, etc., and such configurations are generally known as blister packaging or "push-through" packaging.

The terms "blister component", "blister packaging" or "push-through packaging", as used herein, refer to multi-layer thermoplastic film or a roll of multilayer thermoplastic film, both of which may be thermoformed, partially thermoformed or not thermoformed at all. For preparing such packages, generally a first packaging component that may be a thermoplastic film is first processed by vacuum forming or pneumatic forming so as to form blisters or cavities thereon, namely portions having a predetermined contour corresponding to each specific article to be received therein. After the so-blistered film has been solidified, each blister is charged with each piece of the article to be packaged and a second or lidding film is then covered over each blister and sealed to the first film. The second packaging component may be a lidding film that is often a laminate material that can be ruptured by a simple finger-rupture or peeled off from the first film to allow access to a packaged article or product. Conventional materials used for forming the blistered film have included transparent polymers such as polyvinylchloride (PVC), polyvinylidene chloride (PVdC), and polychlorotrifluoroethylene (PCTFE).

Product Contact Layer

The packaging components described herein each include a sealant layer that is a product-contacting layer. The first packaging component includes a sealant layer that includes a first ethylene vinyl copolymer (EVOH) and the second packaging component includes a sealant layer that includes a second ethylene vinyl copolymer (EVOH). The terms "ethylene vinyl alcohol copolymer", "EVOH copolymer", and "EVOH", as used herein, refer to copolymers comprised of repeating units of ethylene and vinyl alcohol. Ethylene vinyl alcohol copolymers may be represented by the general formula: $[(CH_2-CH_2)_n-(CH_2-CH(OH))_m]$. Ethylene vinyl alcohol copolymers may include saponified or hydrolyzed ethylene vinyl acetate copolymers. In commercial grades of EVOH, the extent of saponification is very high, such that the presence of any unsaponified vinyl acetate groups is typically ignored. The EVOH composition is usually expressed in terms of its ethylene content and for commercial grades used in packaging applications, the ethylene content may range from 27 mol percent to 48 mol percent, though even broader compositions are produced for other applications. The first and second EVOH sealant layers may be comprised of a single EVOH grade or of blends of two or more EVOH grades.

EVOH is commercially available in resin form with various percentages of ethylene and there is a direct relationship between ethylene content and melting point. For example, EVOH having a melting point of about 175 degrees Celsius or lower is characteristic of EVOH materials having an ethylene content of 38 mol percent or higher. With increasing ethylene content, the melting point is lowered. Also, EVOH copolymers that have increasing mol percentages of ethylene generally have greater gas permeabilities that are dependent on factors such as relative humidity and the nature of the permeating gas. For EVOH, a melting point of about 158 degrees Celsius corresponds to an ethylene content of 48 mol percent and a melting point of about 175 degrees Celsius corresponds to an ethylene content of 38 mol percent has. EVOH copolymers having lower or higher ethylene contents may also be employed. It is expected that processability and orientation would be facilitated at higher ethylene contents; however, gas permeabilities, particularly with respect to oxygen, may become undesirably high for certain packaging applications that are sensitive to microbial growth in the presence of oxygen. Conversely lower ethylene contents may have lower gas permeabilities, but processability and orientation may be more difficult. One source of suitable EVOH copolymers to be used as sealant layer material is available from Kuraray America, Inc, Houston, TX, USA, under the trade name of EVAL.

It is believed that the EVOH copolymers described herein may also be anti-scalping with regard to pharmacological agents. By way of example, EVOH copolymers described herein can be used as product-contacting layers when the product includes one or more of the following non-limiting examples of nicotine, tetrahydrocannabinol (THC), fentanyl, acetylfentanyl, lidocaine, estradiol, clonidine, ethinyl estradiol, oxybutynin, buprenorphine, granisetron, methylphenidate, and scopolamine, or when one or more of these agents are associated with a volatile carrier.

In some embodiments, EVOH copolymers described herein can be used as product-contacting layers when the product includes one or more of nicotine, THC, acetylfentanyl, and lidocaine. EVOH copolymer layers are shown herein to resist migration of nicotine, THC, acetylfentanyl and lidocaine.

The ethylene content of the first EVOH of the first packaging component may be greater than 38 mol percent. That is, the ethylene content may be 39 mol percent, 40 mol percent, 41 mol percent, 42 mol percent, 43 mol percent. 44 mol percent, 45 mol percent, 46 mol percent, 47 mol percent, 48 mol percent, or any mol percent in between or greater than 48 mol percent. In another embodiment, the ethylene content of the first EVOH may be 48 mol percent. In a further embodiment, the ethylene content of the first EVOH may be greater than 48 mol percent.

The ethylene content of the second EVOH of the second packaging component may be equal to or less than 38 mol percent. That is, the ethylene content may be 38 mol percent, 37 mol percent, 36 mol percent, 35 mol percent, 34 mol percent, 32 mol percent, 31 mol percent, 30 mol percent, 29 mol percent, 28 mol percent, or any mol percent in between or less than 28 mol percent. In another embodiment, the ethylene content of the second EVOH may be 28 mol percent. In a further embodiment, the ethylene content of the second EVOH may be less than 28 mol percent.

The EVOH containing sealant layers are shown herein to resist the migration of nicotine while providing good seal properties to the packaging, for example, hermetic seals. In an embodiment, the first EVOH of the first packaging component comprises an ethylene content greater than 38 mol percent and the second EVOH of the second packaging component comprises an ethylene content of 38 mol percent or less. In another embodiment, the first EVOH of the first packaging component comprises an ethylene content of 48 mol percent and the second EVOH of the second packaging component comprises an ethylene content of 38 mol percent.

Any suitable process can be used to seal packaging having the product-contacting EVOH layers described herein. For example, the product-contacting sealant layers, in some embodiments, can be sealed using ultrasonic sealing techniques as generally known in the art. In some embodiments, one or more strips of a cold sealing coating can be applied to the product-contacting sealant layers. However, the entire product-contacting sealant layer cannot be coated with a cold sealing coating because the product-contacting layer would not be available for contact with the packaged product. Because the packaged product may contact cold seal material, even if the cold seal coating is limited to regions of the seal, cold sealing is generally not preferred. Preferably, the EVOH product-contacting sealant layers are heat sealed. That is, the layers are capable of fusion bonding by conventional heating which generates sufficient heat on at least one film contact surface for conduction to the contiguous film contact surface and formation of a bond interface therebetween without loss of the film integrity. The bond interface between contiguous inner layers preferably has sufficient physical strength to withstand the packaging process and subsequent handling. Advantageously, the bond interface is preferably sufficiently thermally stable to prevent gas or liquid leakage therethrough when exposed to above or below ambient temperatures, e.g., during one or more of the following: packaging operations, storage, handling, and transport. That is, the bond interface or seal may be a hermetic seal. The terms "hermetic seal" or "hermetically sealed", as used herein, refer to a seal that is maintained against the flow of air or fluid, in other words, an airtight or liquid proof seal.

The term "heat seal", as used herein, refers to the union of a surface (or portion thereof) of one film to a surface (or portion thereof) of another film or two different portions of a surface of the same film using heat and pressure. The heat seal is achieved by bringing two surfaces or portions of a surface into contact, or at least close proximity, with one another and then applying sufficient heat and pressure to a predetermined area of the two surfaces to cause the contacting surfaces to become molten and intermix with one another, thereby forming an essentially inseparable fusion bond between the two surfaces in the predetermined area when the heat and pressure are removed therefrom and the area is allowed to cool.

A critical aspect of heat seals with respect to the present disclosure is the seal initiation temperature. The term, "seal initiation temperature", as used herein, refers to the first temperature above ambient at which a seal can form by applying a given temperature and pressure to a given thickness of packaging film for a given length of time. A first packaging component comprising a first EVOH and a second packaging component comprising a second EVOH, as disclosed herein, when heat sealed to each other, provide improved seal initiation temperatures. For example, a heat seal strength of at least 525 Newton/m (3 pounds-force/inch) may be desired for packages of the present disclosure. In some embodiments, the first and second packaging components have a seal initiation temperature within a range from 163 degrees Celsius to 193 degrees Celsius (330 degrees Fahrenheit to 380 degrees Fahrenheit). The packaging components of the present disclosure are able to achieve desired heat seal strengths at lower seal initiation temperatures than comparative packaging components.

The seal initiation temperatures for the first and second packaging components as disclosed herein are unexpected. For example, one of skill in the art would expect that a first EVOH and a second EVOH that have the same, relatively high ethylene content (e.g., 48 mol percent) to achieve a desired heat seal strength at a lower seal initiation temperature due to the relatively lower melting point (158 degrees Celsius) of the first and second EVOH. The first and second EVOH begin to melt, intermingle and fuse with each other when forming the heat seal. Comparatively, one would expect that a first EVOH and a second EVOH that have the same, relatively low ethylene content (e.g., 38 mol percent) to achieve a desired heat seal strength at a higher seal initiation temperature due to the relatively higher melting point (175 degrees Celsius) of the first and second EVOH. The first and second EVOH beginning to melt, intermingle and fuse with each other when forming the heat seal. One of skill in the art would not expect that a first EVOH and a second EVOH of differing ethylene content (38 mol percent and 48 mol percent, respectively) to achieve desired seal strengths at a lower seal initiation temperature than a first and second EVOH having the same ethylene content (38 mol percent). While not being bound by theory, one of skill in the art would expect that the difference in the melting points of the first and second EVOH of differing ethylene content (38 mol percent and 48 mol percent, respectively) would not allow each of the first and second EVOHs to melt and intermingle until a relatively higher seal initiation temperature is reached. As such, the heat seal strengths of the first and second EVOH copolymers that have differing ethylene content, as disclosed in the present application, are surprising. The ethylene content for each the first and second EVOH for the present disclosure reflect ranges that provide suitable sealability, such as being heat sealable in a temperature range from 163 degrees Celsius to 193 degrees Celsius.

The first packaging component sealant layer and the second packaging component sealant layer can be heat sealed to each other to form a package that includes an interior that can contain a product. The heat seals can be formed at conditions from 143 degrees Celsius to 221 degrees Celsius (290 degrees Fahrenheit to 430 degrees Fahrenheit) with a 1 second dwell time at a pressure of 0.2 MPa (30 psi) by methods as generally known by one having skill in the art. The heat seal strengths of the first packaging component sealant layer to the second packaging component sealant layer are determined according to ASTM F88.

It will be understood that some of the aforementioned properties can be affected by the thickness of the product-contacting sealant layer, which can be of any suitable thickness. For example, the thickness of a product-contacting sealant layer may advantageously be less than 0.45 mil (10.16 microns) and greater than 0.05 mil (1.27 microns), including 0.10, 0.15, 0.20, 0.25, 0.30, 0.40, or 0.45 mil thick.

In various embodiments, the product-contacting sealant layer of the first packaging component comprises at least 95 wt. percent of the first EVOH copolymer, more preferably at least 96 weight (wt.) percent, 97 wt. percent, 98 wt. percent, 99 wt. percent, or 100 wt. percent, and any amount there between. The first EVOH may be blended with up to 5 wt. percent, preferably up to 2.5 wt. percent and more preferably up to 1 wt. percent of compatible polymers, colorants, processing aids and the like. Use of these polymers and components in a blend with the EVOH may undesirably affect the anti-scalping properties of this layer and addition of amounts above 5 wt. percent may be unacceptable for many applications of the packaging of drugs or drug articles such as transdermal patches e.g. nicotine patches or fentanyl patches, or containers that contain drugs or drug articles.

In various embodiments, the product-contacting sealant layer of the second packaging component comprises at least 95 wt. percent of a second EVOH copolymer, more preferably at least 96 wt. percent, 97 wt. percent, 98 wt. percent, 99 wt. percent, or 100 wt. percent, and any amount there between. A second EVOH may be blended with up to 5 wt. percent, preferably up to 2.5 wt. percent and more preferably up to 1 wt. percent of compatible polymers, colorants, processing aids and the like. Use of these polymers and components in a blend with the EVOH may undesirably affect the anti-scalping properties of this layer and addition of amounts above 5 wt. percent may be unacceptable for the packaging of drugs or drug articles.

The first packaging component and the second packaging component described herein may include one or more additional, optional layers, such as one or more barrier layers, an exterior layer which can be an abuse-resistant outer layer, or one or more intermediate layers, which may include one or more tie layers.

Barrier Layer

If included, a barrier layer preferably functions both as a gas barrier layer and as a moisture barrier layer, although these functions may be provided by separate layers. A gas barrier layer is preferably an oxygen barrier layer and is preferably a core layer positioned between and protected by surface layers. For example, an oxygen barrier layer can be in contact with a first surface layer and an adhesive layer or may be sandwiched between two tie layers and/or two surface layers. A packaging component may comprise an oxygen barrier having an oxygen permeability that is low enough to prevent oxidation of oxygen sensitive articles and substances to be packaged in the film; for example, oxygen sensitive articles such as products, that include for example, nicotine or fentanyl, or oxygen sensitive collection samples such as blood, which may be collected, for example, in a microcassette device. An oxygen barrier layer may comprise a metal or metal oxide layer, or EVOH, polyalkylene carbonate, polyacrylonitrile, polyethylene furanoate (PEF), polyglycolic acid (PGA), nanocomposite, although oxygen barrier layers comprising polyvinylidene chloride-vinyl chloride copolymer (PVdC or VDC-VC) or vinylidene chloride-methyl acrylate copolymer (VDC-MA) as well as blends thereof, can also be used. The term "nanocomposite", as used herein, refers to a mixture that includes a polymer, or copolymer having dispersed therein a plurality of individual platelets obtained from an exfoliated modified clay and having oxygen barrier properties. Examples of suitable metal and metal oxide layers include foils and deposited metals, such as aluminum foil, aluminum oxide, silicon oxide, metalized polyethylene terephthalate, and the like.

Preferably a multilayer packaging component in accordance with the present disclosure will have an oxygen transmission rate (OTR) of less than or equal to 10, more preferably less than 1, more preferably less than 0.1, more so preferably less than 0.01, and most preferably less than 0.001 cc/m$^2$/24 hours at Room Temperature (RT) (23 degrees Celsius), 0 percent relative humidity (RH) and 1 atmosphere as measured according to ASTM F1927. In an embodiment, the OTR may be from 0.1 cc/m$^2$/24 hours at 23 degrees Celsius, 0 percent RH and 1 atmosphere. In other embodiments, the OTR may be from 0.15 cc/m$^2$/24 hours to 0.25 cc/m$^2$/24 hours at 23 degrees Celsius, 0 percent RH and 1 atmosphere.

A moisture barrier is preferably selected to limit or slow the ingress of moisture. Packaging that includes a moisture barrier can prevent a product from losing moisture content. For example, a film may comprise a moisture barrier having a moisture permeability that is low enough to prevent deleterious effects upon packaged articles such as transdermal drug patches or other moisture sensitive products. In some embodiments, the moisture barrier may be composed of, but not limited to metal, metal oxide depositions, such as aluminum oxide or silicon oxide, and polymers such as, fluoropolymers, for example, PVdC or PCTFE, and polyolefins, for example, HDPE, polypropylene (PP) and COC.

The term "polyolefin", as used herein, refers to homopolymers or copolymers, including, for example, bipolymers, terpolymers, etc., having a methylene linkage between monomer units which may be formed by any method known to those having skill in the art. Non-limiting examples include low density polyetheylene (LDPE), high density polyethylene (HDPE), ethylene alpha-olefin copolymers (EAO) preferably utilizing butene-1, hexene-1, or octene-1 comonomer with a predominate ethylene comonomer portion and including, e.g., linear low density polyethylene (LLDPE), very low density polyethylene (VLDPE), metallocene-catalyzed linear low density polyethylene (mLLDPE), plastomers, and elastomers, copolymers of ethylene and polar groups such as vinyl acetate (VA), methyl acrylate (MA), or acrylic acid (AA), e.g., ethylene vinyl acetate copolymer (EVA) or ethylene methyl acrylate copolymer (EMA) or ethylene acrylic acid copolymer (EAA), ionomers, functional group-modified polymers including, e.g., anhydride-modified polyolefins. Propylene and butene-1 homopolymers including polypropylene and polybutene-1 as well as copolymers of varying proportions of ethylene, propylene and butene-1 are useful.

A preferred packaging component according to various embodiments will have a water or moisture transmission rate (WVTR), as determined by ASTM F1249, of less than 0.1, or preferably 0.01, and more preferably less than 0.001 g/m$^2$/24 hours at 38 degrees Celsius (100 degrees Fahrenheit) and 90 percent RH. In an embodiment, the WVTR may be 0.1 g/m$^2$/24 hours at 38 degrees Celsius and 90 percent RH. In other embodiments, the WVTR may be from 0.01 g/m$^2$/24 hours to 0.04 g/m$^2$/24 hours at 38 degrees Celsius and 90 percent. RH.

The term "polyester", as used herein, refers to synthetic homopolymers and copolymers having ester linkages between monomer units which may be formed by condensation polymerization methods. Non-limiting examples include poly(ethylene terephthalate), poly(ethylene isophthalate), poly(butylene terephthalate), poly(ethylene naphthalate), poly(butylene succinate) (PBS), poly(butylene succinate-co-butylene adipate) (PBSA), and blends thereof.

The term "polyester" as used herein refers to homopolymers and copolymers having recurring ester linkages which may be formed by any method known in the art. Recurring ester linkages may be formed by the reaction of one or more diols with one or more diacids. Non-limiting examples of suitable diols include ethylene glycol, diethylene glycol, 1,3-propanediol, 1,4-butanediol, resorcinol, 1,4-cyclohexanedimethanol, 2,2,4,4-tetramethyl-1,3-cyclobutanediol, and polyoxytetramethylene glycol. Non-limiting examples of suitable diacids include terephthalic acid, isophthalic acid, 2,6-naphthalene dicarboxylic acid, 2,5-furandicarboxylic acid, 1,4-cyclohexane dicarboxylic acid, trimellitic anhydride, succinic acid, adipic acid and azelaic acid.

Non-limiting examples of suitable polyesters include poly (ethylene terephthalate) (PET), poly(ethylene terephthalate-co-cyclohexanedimethanol terephthalate) (PETG), poly (butylene terephthalate) (PBT), poly(ethylene naphthalate) (PEN), poly(ethylene furanoate) (PEF), polypropylene furanoate) (PPF) and poly(butylene adipate-co-terephthalate) (PBAT).

Suitable polyesters may be formed via other reactions. For example, some polyesters may be formed by the ring-opening polymerization of suitable cyclic monomers like lactides to form, for example, polylactic acid) (PLA), glycolides to form, for example, poly(glycolic acid) (PGA) and lactones to form, for example, poly(caprolactone) and poly (butyrolactone). Other suitable polyesters may be formed by the direct condensation reaction of alpha hydroxy acids. For example, PGA may be formed by the condensation reaction of glycolic acid. Further, suitable polyesters may be synthesized by microorganisms. Examples of suitable polyesters include various poly(hydroxy alkanoates) like poly(hydroxy butyrate) (PHB) and poly(hydroxy valerate) (PHV).

The terms "polyimide", "PA" or "nylon", as used herein, refer to homopolymers or copolymers having recurring amide linkages and may be formed by any method known in the art. Recurring amide linkages may be formed by the reaction of one or more diamines and one or more diacids. Non-limiting examples of suitable diamines include 1,4-diamino butane, hexamethylene diamine, decamethylene diamine, metaxylylene diamine and isophorone diamine. Non-limiting examples of suitable diacids include terephthalic add, isophthalic add, 2,5-furandicarboxylic acid, succinic acid, adipic acid, azelaic acid, capric acid and lauric acid. Polyamides may also be formed by the ring-opening polymerization of suitable cyclic lactams like ε-caprolactam, ω-undecanolactam and ω-dodecalactam.

Non-limiting examples of suitable polyamides include poly(ε-caprolactam) (nylon 6), poly(ω-undecanolactam) (nylon 11), poly(ω-dodecalactam) (nylon 12), poly(hexamethylene adipamide) (nylon 6,6), poly(hexamethylene adipamide-co-caprolactam) (nylon 66/6), poly(caprolactam-co-hexamethylene adipamide) (nylon 6/66), poly(caprolactam-co-hexamethylene azelamide) (nylon 6/69), poly(m-xylylene adipamide) (MXD6) and poly(hexamethylene terephthalamide-co-hexamethylene isophthalamide) (nylon 6I/6T).

It should be understood that the barrier layer(s) and the anti-scalping product-contacting sealant layer may be the same compositionally or may be different. For example, EVOH is known to provide good anti-scalping and oxygen barrier properties. In an embodiment, EVOH may function as both an anti-scalper and an oxygen barrier in the same layer of the packaging component. In another embodiment, the packaging component may include one layer of EVOH intended to provide anti-scalping and another layer of EVOH intended to provide oxygen barrier. In other embodiments, the packaging component may include more than two layers of EVOH.

It is desirable that the thickness of the barrier layer be selected to provide the desired combination of the performance properties sought, e.g., with respect to anti-scalping, oxygen permeability, delamination resistance, and water barrier properties. Oxygen barrier polymers tend to be relatively expensive and therefore it is expected that less costly resins will be used in other layers to impart desirable properties once a suitable thickness is used to achieve the desired gas barrier property for the film layer combination. For example, the thickness of an oxygen barrier layer that is separate from the anti-scalping layer may advantageously be from 1.27 microns (0.05 mil) to 11.43 microns (0.45 mil), or may be 2.54, 5.08, 6.35, 7.62, 10.16, or 11.43 microns thick or any thickness there between.

Exterior Protective Layer

The packaging components described herein may include an exterior layer. The exterior surface of the packaging components preferably has desirable optical properties and may preferably have high gloss. Also, it preferably withstands contact with sharp objects and provides abrasion resistance, and for these reasons, it is often termed the abuse-resistant or protective layer. As the exterior surface layer of the packaging component, this layer most often is also the exterior layer of any package, pouch, blister pack, or other container made from a first and second packaging component as described herein, and is therefore subject to handling and abuse, e.g., from equipment during packaging, and from rubbing against other packages and shipping containers and storage shelves during transport and storage. This contact causes abrasive forces, stresses and pressures which may abrade away the film causing defects to printing, diminished optical characteristics or even punctures or breaches in the integrity of the package. Therefore, the exterior surface layer is typically made from materials chosen to be resistant to abrasive and puncture forces and other stresses and abuse which the packaging may encounter during use. Suitable stiffness, flexibility, flex crack resistance, modulus, tensile strength, coefficient of friction, printability, and optical properties are also frequently designed into exterior layers by suitable choice of materials. This layer may also be chosen to have characteristics suitable for creating desired heat seals which may include resistance to burn through, e.g., by impulse sealers or may be used as a heat-sealing surface in certain package embodiments, e.g., using overlap seals. The exterior layer may impart resistance to opening by children, e.g., preventing the package from being opened by a child's bite. A preferred exterior child-resistant layer comprises polyester film, preferably polyethylene terephthalate, preferably at least 22.86 microns (0.9 mil) in thickness. Suitable exterior surface layers may comprise: paper, oriented polyester, amorphous polyester, polyamide, polyolefin, semi-aromatic polyesters, glycol-modified polyethylene terephthalate, aliphatic polyesters, polyhydroxyalkonates, polystyrenes, high impact polystyrene, general purpose polystyrene, styrene block copolymer (SBC), cast or oriented nylon, polypropylene, or copolymers, or blends thereof. Oriented films of this or any other layer may be either uni-axially or bi-axially oriented. The exterior layer thickness is typically 12.7 microns to 50.8 microns (0.5 mil to 2.0 mil). Thinner layers may be less effective for abuse resistance, however thicker layers, though more expensive, may advantageously be used to produce films having unique highly desirable puncture resistance and/or abuse resistance properties.

Intermediate Layer

An intermediate layer is any layer between the exterior layer and the interior product-contacting sealant layer and may include moisture barrier layers, oxygen barrier layers, tie layers or layers having functional attributes useful for the packaging components or their intended uses. Intermediate layers may be used to improve, impart or otherwise modify a multitude of characteristics: e.g., printability for trap-printed structures, machinability, tensile properties, flexibility, stiffness, bulk, modulus, designed delamination, easy-opening features, tear properties, strength, elongation, optical, moisture barrier, oxygen or other gas barrier, radiation selection or barrier, e.g., to ultraviolet wavelengths, etc. Suitable intermediate layers may include: adhesives, adhesive polymers, paper, oriented polyester, amorphous polyester, polyamide, polyolefin, nylon, polypropylene, or copolymers, or blends thereof. In some embodiments, the intermediate layer may include HDPE, a blend of HDPE (HDPE-blend), a high density polyethylene nucleation additive and optionally, a hydrocarbon resin, or a bimodal HDPE having a distribution of a low molecular weight region and a high molecular weight region. The intermediate layer(s) may be of any suitable thickness from 2.54 microns to 177.8 microns (0.1 mil to 7 mil) or may even be omitted for use in certain applications.

The term "nucleation additive", as used herein, refers to a material that increases high density polyethylene crystallinity and/or beneficially alters the size, shape or orientation of high density polyethylene crystals such that WVTR is reduced as a result of its incorporation into HDPE. Non-limiting examples of nucleation additives include chalk, talc, clay, kaolin, silicates and the like, and organic agents such as salts of aliphatic or aromatic carboxylic acids, aromatic salts, metallic salts of aromatic phosphorous compounds, quinaridones, and aromatic amides. Further examples include zinc glycerolate, calcium glycerol late, calcium hexahydrophthalate, zinc hexahydrophthalate, salts and the like, and mixtures thereof. The nucleation additive may be present in each intermediate layer of HDPE in an amount from 0.2 percent to 3.5 percent by weight relative to the total weight of the layer.

The term "hydrocarbon resin", as used herein, refers to a product produced by polymerization from coal tar, petroleum, and turpentine feed stocks, as defined by ISO Standard 472, "Plastics—Vocabulary" incorporated by reference herein to the extent that it teaches hydrocarbon resins. A hydrocarbon resin may comprise any of those hydrocarbon resins disclosed in U.S. Pat. No. 6,432,496 or in U.S. Patent Application 2008/0286547, both of which are incorporated in their entireties in this application by this reference. More specifically, as a non-limiting example, the hydrocarbon resin may include petroleum resins, terpene resins, styrene resins, cyclopentadiene resins, saturated alicyclic resins or mixtures of such resins. Additionally, as a non-limiting example, the hydrocarbon resin may comprise hydrocarbon resin derived from the polymerization of olefin feeds rich in dicyclopentadiene (DCPD), from the polymerization of olefin feeds produced in the petroleum cracking process (such as crude C9 feed streams), from the polymerization of pure monomers (such as styrene, α-methylstyrene, 4-methylstyrene, vinyltoluene or any combination of these or similar pure monomer feedstocks), from the polymerization of terpene olefins (such as α-pinene, β-pinene or d-limonene) or from a combination of such. The hydrocarbon resin may be fully or partially hydrogenated. Specific examples of hydrocarbon resins include but are not limited to PLAS-TOLYN R1140 Hydrocarbon Resin available from Eastman Chemical Company (Kingsport, TN, USA), REGALITE T1140 available from Eastman Chemical Company, ARKON P-140 available from Arakawa Chemical Industries, Limited (Osaka, Japan) and PICCOLYTE S135 Polyterpene Resins available from Pinova, Inc. (Brunswick, GA, USA). The hydrocarbon resin may be present in each intermediate layer from 3 percent to 16 percent by weight relative to the total weight of the layer.

Tie Layer

A multilayer packaging component can include one or more adhesive layers, also known in the art as "tie layers," which can be selected to promote the adherence of adjacent layers to one another in a multilayer film and prevent undesirable delamination. A multifunctional layer is preferably formulated to aid in the adherence of one layer to another layer without the need of using separate adhesives by virtue of the compatibility of the materials in that layer to the first and second layers. Alternatively, the tie layers can serve as an intermediary to different adhesives that are compatible with different layers or can serve to aid in the adherence of one layer to another layer without the need of using a separate adhesive while serving as an intermediary between a different layer and an adhesive. It should be understood that tie layers, as generally known by a person of ordinary skill in the art, may be incorporated into the packaging components as appropriate.

In some embodiments, adhesive layers comprise materials found in both the first and second layers that the adhesive layer adheres together. In some embodiments, a multilayer film comprises a first adhesive layer positioned between and in direct contact with an exterior layer and a product-contacting layer. In some embodiments, a multilayer film comprises a first adhesive layer positioned between and in direct contact with a product-contacting layer and a metal or metal oxide layer. The metal or metal oxide layer can be a foil or deposited layer. The multilayer film may further include a polyolefin layer, such as a polyethylene layer, in contact with the metal or metal oxide layer and an exterior protective layer, such as a layer comprising polyethylene terephthalate.

Multilayer films can comprise any suitable number of tie or adhesive layers of any suitable composition. Various adhesive layers are formulated and positioned to provide a desired level of adhesive between specific layers of the film according to the composition of the layers contacted by the tie layers.

In embodiments where the layers comprise compatible polymers, the layers can be coextruded or laminated by heat rather than adhered via a tie layer.

Optional Additives to Layers

Various additives may be included in the polymers utilized in one or more of the exterior, interior and intermediate or tie layers of packaging comprising the same. Non-limiting examples of optional additives include anti-block agents, slip agents, stabilizing agents, release agents, lubricating agents, anti-oxidants, photo-initiators, primers, colorants, and other additives known to and used by a person of ordinary skill in the art without undue experimentation. The use of optional additives varies depending on the equipment, materials, desired aesthetics, etc.

Methods of Manufacture

The packaging components may include materials that are monolayer (product-contacting sealant layer) or multilayer films. The films described herein can be made by any suitable process as generally known by one of skill in the art. Examples of such processes include cast or blown film processes. Further, the films are polymeric or combinations of polymeric materials and non-polymeric materials like aluminum foil, paper, etc., and may be used to form flexible, semi-rigid, or rigid packaging components.

In some embodiments, the product-contacting sealant layer may be attached to a non-polymeric material. Non-limiting examples may include foil, paper, plant fiber-containing material, and glass. The term "attached", as used herein, refers to materials adhering two surfaces to one another, such as the planar surfaces of two film layers. In an embodiment, the EVOH copolymer product-contacting sealant layer may be coated onto a non-polymeric material such as aluminum foil, where the resulting packaging component may be a foil lid. When the EVOH copolymer product-contacting layer is coated onto a substrate to format a packaging component, the coating may be continuous or discontinuous.

In another embodiment, the EVOH copolymer product-contacting sealant layer may be laminated onto a monolayer polymeric film or a multilayer polymeric film. The laminating methods include, but are not limited to, thermal lamination, adhesive lamination, extrusion lamination, and extrusion coating. In an embodiment, the EVOH copolymer product-contacting sealant layer may be joined to the remainder of the packaging component by a laminating agent. In an embodiment, the laminating agent may be an extrusion laminating agent where the parameters for such lamination are expected to be set by one skilled in the art without undue experimentation. Further, the laminating agent can be any material and can be added by any known process as long as it does not disrupt the spirit of the disclosure; that is, an EVOH copolymer product-contacting sealant layer that can provide anti-scalping properties without negatively affecting the sealing properties of the first and second packaging components to each other, which also provides oxygen barrier to the package.

In a further embodiment, the packaging component may be produced via a coextrusion that includes an EVOH copolymer product-contacting sealant layer. The packaging components produced via coextrusion may be multilayer thermoplastic films comprising at least 2 or 3 or 4 or 5 or 6 or 7 or 8 or 9 or 10 or 11 or 12 or 13 or more layers. The terms "coextruded", "coextrude", or "coextrusion", as used herein, refer to the process of extruding two or more polymer materials through a single die with two or more orifices arranged so that the extrudates merge and weld together into a laminar structure before chilling (i.e., quenching). Examples of coextrusion methods known in the art include but are not limited to blown film (annular) coextrusion, slot cast coextrusion and extrusion coating. The flat die and slot cast processes include extruding polymer streams through a flat or slot die onto a chilled roll and subsequently winding the film onto a core to form a roll of film for further processing.

The term "blown film", as used herein, refers to a film produced by the blown coextrusion process. In the blown coextrusion process, streams of melt-plastified polymers are forced through an annular die having a central mandrel to form a tubular extrudate. The tubular extrudate may be expanded to a desired wall thickness by a volume of fluid (e.g., air or other gas) entering the hollow interior of the extrudate via the mandrel and then rapidly cooled or quenched by any of various methods known in the art.

The sequence of layers in the packaging component may be palindromic. The term "palindromic", as used herein, refers to a multilayer film, the layers of which are substantially symmetrical. Non-limiting examples of palindromic films are film or sheet having the layer sequence of configurations: A/B/A or A/B/B/A or A/B/C/B/A or A/B/C/D/C/B/A or A/B/C/B/D/B/C/B/A or A/B/E/D/E/B/C/B/E/D/E/B/A, etc. An example of a layer sequence configuration of a non-palindromic film would be A/B/C or A/B/C/A. A palindromic thermoplastic film may be coextruded as a symmetrical cast or blown film using coextrusion methods generally well known in the art. An alternative method of producing palindromic films is by the use of blown coextrusion of non-symmetrical film or sheet structures followed by collapsing the blown bubble around a central core layer.

In some embodiments, the sequence of layers in a packaging component may be non-palindromic.

In an embodiment, a packaging component of the present disclosure may be characterized as a palindromic film formed from a non-symmetrical film having a generic layer sequence configuration of A/B/C which is coextruded by blown film coextrusion techniques and collapsed upon itself to produce a layer sequence configuration of A/B/C/B/A where tie layers are used as appropriate. One of the A layers will form the product-contacting sealant layer. In this embodiment, the packaging component includes a film where layer A is an exterior layer comprising an EVOH copolymer, layer B is an intermediate layer comprising a HDPE, a blend of HDPE (HDPE-Blend), a high density polyethylene nucleation additive and optionally, a hydrocarbon resin, or a bimodal HDPE having a distribution of a low molecular weight region and a high molecular weight region (HDPE-Bimodal), and has a thickness of between 38.1 microns to 190.5 microns (1.5 mil to 7.5 mil), and layer C is a central core layer. The central core layer C may be any suitable polymeric material which can be blown coextruded and collapsed upon itself. One non-limiting example of such materials is ethylene vinyl acetate copolymer (EVA). It should be understood that tie layers may be incorporated into the layer sequence as appropriate. In an embodiment, the central core layer comprises an ethylene vinyl acetate copolymer (EVA) having a 12 wt. percent of vinyl acetate content. Non-limiting examples of EVA include ESCORENE Ultra LD 705.MJ available from ExxonMobil Chemical Company, Houston, TX, USA, ESCORENE Ultra LD 768.MJ available from ExxonMobil Chemical Company, and ATEVA 2861AU available from Celanese Corporation, Edmonton, Alberta, CA.

In another embodiment, the packaging component of the present disclosure may be characterized as a non-palindromic film having a layer sequence configuration of A/B/C/B/D which is coextruded by blown film coextrusion techniques, incorporates tie layers as appropriate, and is not collapsed upon itself. In this embodiment, the packaging component includes a film where layer A is an exterior layer comprising a EVOH copolymer, layer B is an intermediate layer comprising a HDPE, a HDPE-Blend, high density polyethylene nucleation additive and optionally, a hydrocarbon resin, or a HDPE-Bimodal, and has a thickness of between 38.1 microns to 190.5 microns (1.5 mil to 7.5 mil), layer C is a central core layer, and D is an exterior layer comprising a different material than layer A and is selected from the group consisting of polypropylene (PP), high impact polystyrene (HIPS), general purpose polystyrene (GPPS), styrene block copolymer (SBC), polyethylene terephthalate (PET), amorphous polyethylene terephthalate (APET), glycol-modified polyethylene terephthalate PETG) and polylactic acid (PLA). Core layer C may be any thermoplastic material. In one preferred embodiment, core layer C comprises ethylene vinyl acetate copolymer (EVA).

Non-limiting examples of layer sequences and general layer compositions, with tie layers incorporated appropriately, include: EVOH/HDPE/EVA/HDPE/EVOH; EVOH/HDPE-Blend/EVA/HDPE-Blend/EVOH; EVOH/HDPE-Bimodal/EVA/HDPE-Bimodal/EVOH; EVOH/HDPE/EVA/HDPE/PP; EVOH/HDPE-Blend/EVA/HDPE-Blend/PP; EVOH/HDPE-Bimodal/EVA/HDPE-Bimodal/PP; EVOH/

HDPE/EVA/HDPE/PETG; EVOH/HDPE-Blend/EVA/HDPE-Blend/PETG; EVOH/HDPE-Bimodal/EVA/HDPE-Bimodal/PETG; EVOH/HDPE/EVA/HDPE/APET; EVOH/HDPE-Blend/EVA/HDPE-Blend/APET; EVOH/HDPE-Bimodal/EVA/HDPE-Bimodal/APET; EVOH/HDPE/EVA/HDPE/PET; EVOH/HDPE-Blend/EVA/HDPE-Blend/PET; EVOH/HDPE-Bimodal/EVA/HDPE-Bimodal/PET; EVOH/HDPE/EVA/HDPE/OPET; EVOH/HDPE-Blend/EVA/HDPE-Blend/OPET; EVOH/HDPE-Bimodal/EVA/HDPE-Bimodal/OPET; EVOH/HDPE/EVA/HDPE/PLA; EVOH/HDPE-Blend/EVA/HDPE-Blend/PLA; EVOH/HDPE-Bimodal/EVA/HDPE-Bimodal PLA; EVOH/HDPE/EVA/HDPE/HIPS; EVOH/HDPE-Blend/EVA/HDPE-Blend/HIPS; EVOH/HDPE-Bimodal/EVA/HDPE-Bimodal/HIPS; EVOH/HDPE EVA/HDPE/GPPS; EVOH/HDPE-Blend/EVA/HDPE-Blend/GPPS; EVOH/HDPE-Bimodal/EVA/HDPE-Bimodal/GPPS; EVOH/HDPE/EVA/HDPE SBC; EVOH/HDPE-Blend/EVA/HDPE-Blend/SBC; and EVOH/HDPE-Bimodal/EVA/HDPE-Bimodal/SBC.

It should be understood, that in some embodiments, the packaging components may further include a gas barrier layer, a moisture barrier layer, adhesive (tie) layers, or other layers as applicable for the final application of the package.

Adhesives useful in the present disclosure include permanent adhesives, modified polymer adhesives and polymer resins commonly available from many commercial sources. It is contemplated that acrylic and anhydride modified polymers may be employed as well as many adhesives which may be selected depending upon other material selections used in other functional layers such as the oxygen and/or moisture barrier layer(s) as well as the exterior abuse resistant or protecting layer as well as the EVOH copolymer containing product-contacting, sealant layer.

Additives and processing aides, natural and synthetic colorants, pigments and dye, fillers such as calcium carbonate or carbon black, and antimicrobial agents may be incorporated into or coated onto one or more layers of the multilayer films of the present disclosure.

Packaging Component Thickness

Preferably, the first packaging component and the second packaging component each have a total thickness of less than 762 microns (30 mil), more preferably each of the packaging components have a total thickness from 25.2 microns to 762 microns (1.0 mil to 30 mil). Advantageously, many embodiments may have a thickness from 25.2 microns to 381 microns (1 mil to 15 mil), other embodiments may be from 50.8 microns to 254 microns (2 mil to 10 mil), and others may be from 76.2 microns to 127 microns (3 mil to 5 mil). For example, first or second packaging components that comprise multilayer films or any single layer of a multilayer film can have any suitable thicknesses, preferably from 25.2 microns to 508 microns, or any increment of 2.54 microns or 0.254 microns (0.1 mil or 0.01 mil) therebetween. Suitable films for the blister component of a blister pack may be, but not limited to, from 203 microns to 508 microns (8 mil to 20 mil) after forming. In some instances, the film thickness may be from 10 percent to 100 percent of the original film thickness after forming due to the various draw on the film to form the appropriate cavity for the given product. Although suitable films for packaging drug patches as thick as 101.6 microns (4 mil) or higher, or as thin as 25.4 microns (1 mil) or less may be made, it is expected that the most common films will be between 51 microns to 102 microns (2 mil to 4 mil). Such films may have good abuse resistance and machinability.

Packaged Product

Any product for which scalping may be a concern can be packaged with a first and second packaging component as described herein. In various embodiments, the product includes a pharmaceutical product or may include pharmaceutical products and one or more pharmaceutical or excipients. Excipients that may be included in various types of pharmaceutical products are generally known to those of ordinary skill in the pharmaceutical arts, some of which are described in Remington: The Science and Practice of Pharmacy, $22^{nd}$ edition, Loyd V. Allen, Jr. (editor), Pharmaceutical Press, September 2012.

A pharmaceutical product for packaging in a first and second packaging component as described herein can include any suitable pharmaceutical active agent. In some embodiments, the pharmaceutical active agent is selected from the group consisting of acetylfentanly, fentanyl, nicotine, lidocaine, estradiol, clonidine, ethinyl estradiol, oxybutynin, buprenorphine, granisitron, methylphenidate, scopolamine, and tetrahydrocannabinol. In some embodiments, one or more of the listed pharmaceutical active agents or excipients are included in a transdermal patch. In some embodiments, one or more of the listed pharmaceutical active agents or excipients are included within a blister pack. Typical contents, or products, for various embodiments of the disclosed packaging may include, for example, thin strips of dissolvable material for oral administration, as well as articles for collecting or administering a physiologically active substance, e.g., a microdiffusion cassette, or vials or cartridges that contain pharmaceutical active agents, e.g., a replacement cartridge for electronic cigarettes.

A pharmaceutical product can be packaged in a first and second packaging component as described herein in any suitable manner. In some embodiments, a pharmaceutical product is packaged such that the pharmaceutical active agent is not in contact with a sealant layer of the film. In some embodiments, the pharmaceutical product is packaged such that the pharmaceutical active agent is in contact with the sealant layer of the film. The active agent can be in direct contact with the sealant layer or in indirect contact with the sealant layer.

In some embodiments, the pharmaceutical product comprises a gel, paste. solution or the like, where gel, paste, solution, etc. contains the active ingredient and is in direct contact with the sealant layer.

In some embodiments, the pharmaceutical product includes an active agent or excipient that acts as a carrier for the active agent where the active agent or the carrier has a vapor pressure sufficiently high to cause volatilization of the active agent or carrier to cause the active agent to contact the sealant layer upon storage, even though the product is initially packaged such that active agent is not in direct contact with the sealant layer.

In some embodiments, the pharmaceutical product includes a transdermal patch. Transdermal patches typically have a release liner covering a matrix comprising a pharmaceutical active agent. Accordingly, the pharmaceutical active agent and excipients of a transdermal patch having a release liner may not be in direct contact with the sealant layer of film in which it is packaged. However, at an edge of the release liner, some of the matrix may come into direct contact with the sealant layer and may allow the active agent to be wicked towards the sealant layer. Alternatively, or in addition, the vapor pressure of the active agent or a carrier excipient may be sufficiently high to cause the active agent to contact the sealant layer upon storage.

In some embodiments, the pharmaceutical product is packaged in a first and second packaging component as described herein such that the pharmaceutical active agent is not in contact with the sealant layer. For example, the active agent may be surrounded by a backing and a release liner or may be otherwise contained such that active agent is not in contact with the sealant layer. In such cases, it can still be desirable to have a sealant layer that would be anti-scalping if the active agent were to come into contact with the sealant layer. For example, if the pharmaceutical product includes a release liner configured to prevent contact of the active agent with the sealant layer, the release liner may slip or otherwise partially release during packaging, shipping, storage or the like to expose the active agent to the sealant layer. In another example, the active agent may be contained in a cartridge that is enclosed within a package in the form of a blister pack. The cartridge may crack, leak or fail, thus exposing the active agent to the sealant layer. Even if there is little or no risk that the active agent may be exposed to the sealant layer, it may be desirable for the sealant layer to be anti-scalping for purposes of caution, reassurance, or the like.

When a pharmaceutical product is packaged in a first and second packaging component such that the product-contacting sealant layer of the packaging components is in indirect contact with a pharmaceutical active agent of the product, detectable amounts of the pharmaceutical agent may be present at a surface of the product-contacting layer or migrate into the product-contacting layer upon storage of the product in the packaging film. Any suitable technique can be employed to determine whether a pharmaceutical agent of a pharmaceutical product indirectly contacts a layer of a package in which the produce is sealed. That is, if a detectable amount of the agent is present at a surface of a layer or in a layer of the film of the packaging components, then the pharmaceutical agent is "in contact" with the layer of the film for purposes of the present disclosure. Examples of suitable techniques that can be employed to determine whether a pharmaceutical agent of a pharmaceutical product indirectly contacts a layer of a package in which the product is sealed include Raman spectroscopy, gas chromatography, gas chromatography-mass spectrometry (GCMS), liquid chromatography-mass spectrometry (LCMS), high performance liquid chromatography (HPLC), and the like.

To determine whether a pharmaceutical active agent of a pharmaceutical product is in indirect contact with a sealant layer of the first or second packaging components, the presence of the active agent at or in a sealant layer of the packaging components can be evaluated after the pharmaceutical product has been packaged in the sealed packaging components under storage conditions for an amount of time. The storage conditions and time can be standard storage conditions. The standard storage conditions can be accelerated storage conditions; e.g. at temperatures above room temperature. For example, the storage conditions can be 20 percent relative humidity and a temperature of 38 degrees Celsius (100 degrees Fahrenheit) for 1, 7, 15 or 31 days.

Alternatively, or in addition, to determine whether a pharmaceutical active agent of a pharmaceutical product would be in indirect contact with a sealant layer of the first or second packaging components as described herein, the presence of the active agent at or in a surrogate sealant layer of the packaging components can be evaluated after the pharmaceutical product has been packaged in the surrogate film under standard storage conditions for a standard amount of time. Preferably, the surrogate film is not anti-scalping or is not as anti-scalping as the first or second packaging components as described herein. The product can be packaged and stored in the film containing the surrogate sealant layer in a manner similar to how the pharmaceutical product packaged in the first and second packaging components as described herein would be packaged and stored. If the active agent migrates into the surrogate sealant layer, then the active agent can be considered to be "in contact" with the surrogate layer and would be considered to be "in contact" with a sealant layer of any film in which it was stored, such as the packaging components described herein.

The disclosed package, for example in the form of a pouch or sachet, can further include a tearing aid or tear initiator such as a notch. Examples of tearing aids or tear initiators such as notches, slits, perforations, surface-roughened portions, etc., are described in U.S. Pat. Nos. 4,778,058, 3,608,815, 4,834,245, 4,903,841, 5,613,779, 5,988,489, 6,102,571, 6,106,448, 6,541,086, 7,470,062, and 7,481,581. Such tear initiators may be used on one or more edges of the disclosed package. Further, the package may include child resistant packaging technology such as that described in U.S. Pat. No. 10,071,833, which is hereby incorporated by reference in its entirety, to provide a child-resistant package which is simultaneously easy to open by an adult.

Anti-Scalping

Solubility parameter analysis can be used to describe the extent to which a chemical compound will associate with a polymer matrix. That is, a relationship between a pharmaceutical active agent and the product-contacting layer can be derived. The solubility of the polymer, along with polymer free volume, crystallinity and chain mobility, determines the susceptibility of a given compound to the phenomenon known as scalping. The Hansen Solubility Parameters website (https://www.hansen-solubility.com/HSP-examples/flavor-scalping.php) discusses flavor scalping and its relation to the Hansen Solubility Parameter (HSP) separation distance. The HSP separation distance is based on a spatial representation of the differences in the three Hansen solubility parameters, $\delta_D$ (dispersive interactions), $\delta_P$ (polar interactions) and $\delta_H$ (hydrogen bonding interactions) that characterize both the polymer matrix and the scalped compound. As the separation distance increases, the solubility of the chemical compound in the polymer matrix decreases. Thus, the tendency for a polymer to scalp a compound can be predicted based on the HSP separation distance, $R_a$, with equation (1):

$$R_a = \sqrt{4(\delta_{D_p}-\delta_{D_c})^2+(\delta_{P_p}-\delta_{P_c})^2+(\delta_{H_p}-\delta_{H_c})^2} \quad (1)$$

Where $\delta_{D_p}$=solubility parameter for dispersive interactions (polymer), $\delta_{D_c}$=solubility parameter for dispersive interactions (compound), $\delta_{P_p}$=solubility parameter for polar interactions (polymer), $\delta_{P_c}$=solubility parameter for polar interactions (compound), $\delta_{H_p}$=solubility parameter for hydrogen bonding interactions (polymer), and $\delta_{H_c}$=solubility parameter for hydrogen bonding interactions (compound).

EVOH can be considered as the polymer. The polar and hydrogen bonding effects can vary due to the influence of the hydroxyl groups. With reference to the chemical formula of EVOH, the Yamamoto Molecular Break (Y-MB) method, which is recommended by the Hansen Solubility Parameters and HSPiP Software, can be used to calculate the sets of individual solubility parameters for the combinations of the n and m monomer units, where n+m=1 and 0≤m≤1. Simplified Molecular Input Line Input System (SMILES) notation can be used to describe the chemical compositions for EVOH that are shown in Table 1.

TABLE 1

Individual Hansen Solubility Parameters for EVOH

| Monomer unit ratio | | Ethylene content (mol percent) | $\delta_D$ | $\delta_P$ | $\delta_H$ | $\delta_T$ |
|---|---|---|---|---|---|---|
| $(-CH_2CH_2-)_n$ | $(-CH_2CHOH-)_m$ | | (MPa$^{1/2}$) | | | |
| 0 | 1 | 0   | 18.4 | 9.2 | 25.5 | 32.8 |
| 1 | 3 | 25  | 17.6 | 7.5 | 19.3 | 27.2 |
| 1 | 2 | 33  | 17.4 | 6.9 | 17.2 | 25.4 |
| 2 | 3 | 40  | 17.2 | 6.5 | 15.6 | 24.1 |
| 1 | 1 | 50  | 17.0 | 5.8 | 13.3 | 22.4 |
| 2 | 1 | 67  | 16.8 | 4.2 | 10.0 | 20.0 |
| 3 | 1 | 75  | 16.5 | 3.8 | 7.9  | 18.7 |
| 1 | 0 | 100 | 16.0 | 1.7 | 2.5  | 16.3 |

The HSP information for EVOH can be used with the HSPs for a variety of chemical compounds to assess their susceptibility to scalping by EVOH over its entire compositional range. The HSPiP software can use SMILES notation to define the chemical compounds. The PubChem Open Chemistry Database (https://pubchem.ncbi.nlm.nih.gov/) was used as a consistent source for the SMILES notation strings used as HSPiP inputs for the chemical compounds that are shown in Table 2. It should be understood that these values do not necessarily agree with experimentally determined values or with those determined by other methods.

TABLE 2

Individual Hansen Solubility Parameters for Chemical Compounds

| Compound | $\delta_D$ | $\delta_P$ | $\delta_H$ | $\delta_T$ |
|---|---|---|---|---|
| | (MPa$^{1/2}$) | | | |
| Nicotine | 18.6 | 5.1 | 5.0 | 19.9 |
| Fentanyl | 18.4 | 6.4 | 4.1 | 19.9 |
| Acetylfentanyl | 18.7 | 6.5 | 5.2 | 20.5 |
| Lidocaine | 18.1 | 8.2 | 6.1 | 20.8 |
| Estradiol | 19.0 | 5.0 | 9.6 | 21.9 |
| Ethinyl estradiol | 19.4 | 5.3 | 7.9 | 21.6 |
| Clonidine | 20.7 | 10.6 | 7.8 | 24.5 |
| Oxybutynin | 17.3 | 3.8 | 5.6 | 18.6 |
| Buprenorphine | 18.4 | 4.4 | 7.7 | 20.4 |
| Granisetron | 19.5 | 10.4 | 5.4 | 22.8 |
| Methylphenidate | 18.0 | 3.9 | 5.5 | 19.2 |
| Scopolamine | 17.9 | 6.8 | 9.3 | 21.3 |
| Tetrahydrocannabinol | 17.8 | 1.8 | 4.9 | 18.5 |

Using the data shown in Tables 1 and 2, Equation 1 can be used to calculate the HSP separation distance $R_a$. The calculated values for a nicotine—EVOH system are shown in Table 3.

TABLE 3

$R_a$ for Nicotine - EVOH System

| Ethylene content (mol percent) | $\delta_D$ | $\delta_P$ | $\delta_H$ | $\delta_T$ | $R_a$ |
|---|---|---|---|---|---|
| | (MPa$^{1/2}$) | | | | (MPa$^{1/2}$) |
| 0   | 18.4 | 9.2 | 25.5 | 32.8 | 20.9 |
| 25  | 17.6 | 7.5 | 19.3 | 27.2 | 14.6 |
| 33  | 17.4 | 6.9 | 17.2 | 25.4 | 12.6 |
| 40  | 17.2 | 6.5 | 15.6 | 24.1 | 11.1 |
| 50  | 17.0 | 5.8 | 13.3 | 22.4 | 8.9  |
| 67  | 16.8 | 4.2 | 10.0 | 20.0 | 6.2  |

TABLE 3-continued $R_a$ for Nicotine - EVOH System

| Ethylene content (mol percent) | $\delta_D$ | $\delta_P$ | $\delta_H$ | $\delta_T$ | $R_a$ |
|---|---|---|---|---|---|
| | (MPa$^{1/2}$) | | | | (MPa$^{1/2}$) |
| 75 | 16.5 | 3.8 | 7.9 | 18.7 | 5.3 |
| 100 | 16.0 | 1.7 | 2.5 | 16.3 | 6.7 |
| Nicotine | 18.6 | 5.1 | 5.0 | 19.9 | |

The values indicate that the expected nicotine solubility decreases as the ethylene content of the EVOH increases over most of the EVOH composition range.

An $R_a$ that is equal to or greater than 8 MPa$^{1/2}$ is indicative of compositions where the amount of scalping is expected to be small according to the HSPiP guideline. Further, EVOH compositions of the present disclosure that include from 38 mol percent to 48 mol percent are known to provide acceptable heat seals even when product-contacting layers of different packaging components of disparate ethylene contents are sealed to each other. As such, satisfactory heat seals and acceptable levels of scalping can be expected when the HSP distance, $R_a$, is equal to or greater than 8 MPa$^{1/2}$ and the ethylene content is: 1) equal to 38 mol percent, 2) between 38 mol percent and 48 mol percent, or 3) equal to 48 mol percent. A graphical representation of the $R_a$ (HSP distance) for EVOH at varying ethylene contents against the expected nicotine solubility is shown in FIG. 1.

These calculations can be completed for chemical compounds other than nicotine. Some compounds, e.g., estradiol, ethinyl estradiol, buprenorphine, and scopolamine, do not have an $R_a$ greater than 8 MPa$^{1/2}$ at an ethylene content that is: 1) equal to 38 mol percent, 2) between 38 mol percent and 48 mol percent, or 3) equal to 48 mol percent. However, the performance of the chemical compound and EVOH system may be acceptable because scalping behavior depends on several polymer properties. Similarly, chemical compound and EVOH systems that provide acceptable $R_a$ values may not perform as expected due to the influence of these other polymer properties.

Further, a dimensionless Relative Energy Distance Value (RED) may be defined as:

$$RED = R_a/R_o \qquad (2)$$

It is believed that the RED value provides a thermodynamic indication of how much active agent can be held by the product-contacting layer. $R_o$ is an experimentally determined factor and in HSP flavor scalping examples, $R_o$ is equal to 8 MPa$^{1/2}$. As such, large RED values may indicate that the polymer and chemical compound pairs are sufficiently far apart in the HSP space and that the solubility contribution to scalping is low. For example, a RED value equal to or greater than 1 may indicate that the polymer has low scalping relative to the chemical compound. For purposes of the present disclosure, a chemical compound can be a pharmaceutical active agent or a pharmaceutical composition and is considered to be a pharmaceutical "product". Preferably, the RED values of one or more of the products paired with the EVOH copolymer are 1.0 or greater. More preferably, the RED values are 1.1, 1.2, 1.3, 1.4, 1.5, 1.6, 1.7, 1.8, 1.9, 2.0, 2.1, 2.2, 2.3, 2.4, 2.5, 2.6, or greater. Additionally, RED values for excipients can be obtained generally as described above with regard to the pharmaceutical active agents.

RED values for a pharmaceutical active agent and a product-contacting sealant layer comprising EVOH copolymer can be determined experimentally or by identifying $R_a$ values in existing databases, such as the HSPiP Datasets available at http://hansen-solubility.com/HSPiPDatasets.html. For polymer blends, $R_a$ values of the various polymers forming the blend can be averaged. If a polymer blend contains 95 percent or more of one polymer, e.g., at least 95 percent of an EVOH copolymer, then, for purposes of the present disclosure, the $R_a$ value for the polymer blend can be assumed to be the $R_a$ value of the polymer making up 95 percent or more of the blend.

It is also believed that the glass transition temperature ($T_g$) provides a kinetic indication of the rate at which the active agent will migrate into the product-contacting layer, with higher $T_g$ tending to result in slower kinetics and thus better anti-scalping properties.

The $T_g$ for EVOHs having ethylene content ranging from 32 mol percent to 44 mol percent range from 60 degrees Celsius to 55 degrees Celsius at 0 percent RH, respectively. The $T_g$ was determined using a Perkin Elmer DSC7 apparatus at a programming rate of 10 degrees Celsius per minute and at varying degrees of RH. The $T_g$ for SOARNOL EVOHs having different mol percent ethylene, available from Nippon Gohsei, Düsseldorf, Germany, were measured. Results are shown in Table 4.

TABLE 4

EVOH: Relative Humidity and $T_g$

| Ethylene content (mol percent) | $T_g$ (Celsius) RH (percent) | | | | |
|---|---|---|---|---|---|
| | 0 | 45 | 65 | 72 | 88 | 100 |
| 32 | 60 | 38 | 37 | 16 | — | 3 |
| 38 | 58 | 40 | 37 | 38 | 18 | 6 |
| 44 | 55 | 38 | 36 | 37 | — | 8 |

Thus, EVOH having an ethylene content of 32 mol percent would be expected to have better anti-scalping (lower migration of chemical compound) than an EVOH having an ethylene content of 44 mol percent when $T_g$ is compared at 0 percent RH. Similarly, based on the $T_g$ trend seen with ethylene content of 32 mol percent and 44 mol percent at 0 percent RH, one would expect that an EVOH having an ethylene content of 28 mol percent would have better anti-scalping than an EVOH having an ethylene content of 48 mol percent.

Whether a product-contacting layer of a packaging component performs effectively as an anti-scalping layer can be a subjective determination, with differing amounts of migration of a pharmaceutical active agent into a layer of a film of the packaging component being considered acceptable depending on, among other things, the active agent, the amount that the active agent migrates into layers of other films, and the like. Any suitable technique may be employed to determine whether less active agent has migrated into the product-contacting layer, for example, Raman spectroscopy or gas chromatography, can be used.

For purposes of the present application, the product-contacting layers of first and second packaging components were tested to determine the degree of pharmaceutical active agent or excipient uptake, or migration, in the package. The first and second packaging components as described herein were sealed to include nicotine. Each packaging component including EVOH-containing product-contacting sealant layers exhibited greater resistance to nicotine scalping than the other common product-contacting layers that were tested. For example, the total nicotine migration of the: 1) EVOH-containing product-contacting layers was 0.192 mg, 2) CXB product-contacting layers was 0.217 mg, and 3) PVC product-contacting layers was 3.725 mg; where CXB is a COC (100 wt. percent) sealant layer system on commercially available SKYBLUE blister packaging film.

Figures

Figure 2:
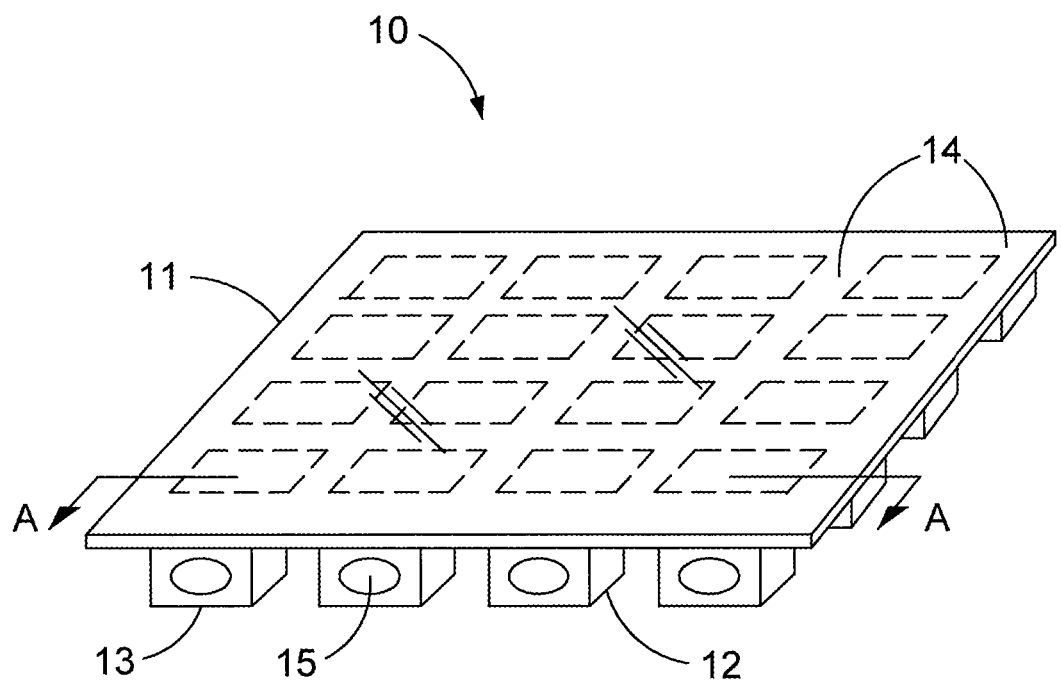
FIG. 2 illustrates a perspective view of an embodiment of a blister package according to the present disclosure.
Figure 3:
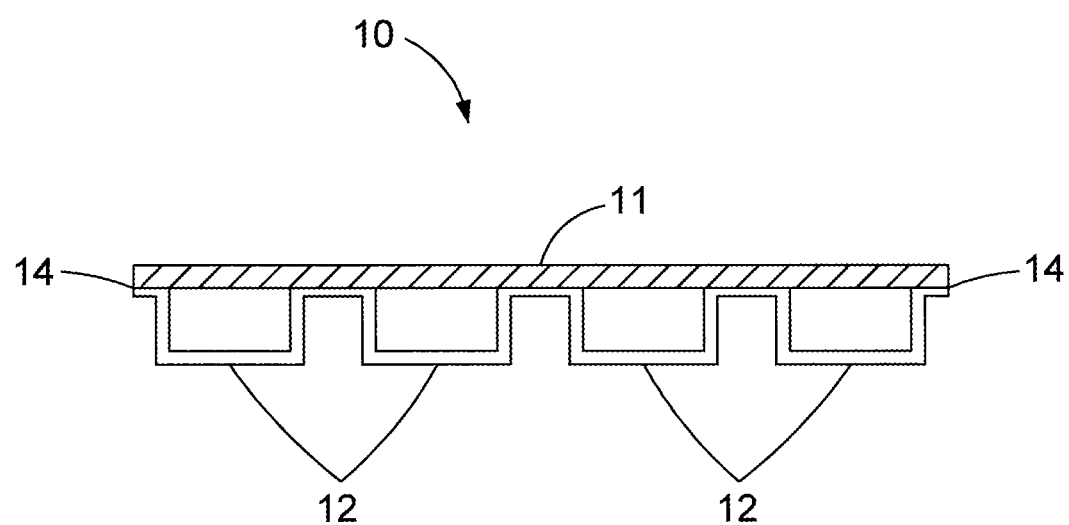
FIG. 3 illustrates a cross-section view of the blister package shown in FIG. 1 along line A-A.

A representative package of the present disclosure is shown as a blister package 10 in FIGS. 2 and 3. Package 10 of the present disclosure includes a first packaging component 11 and a second packaging component 12. The first packaging component 11 is a lidding component. The second packaging component 12 is a thermoformed blister pack and is provided with one or more thermoformed pockets 13. The first packaging component 11 and the second packaging component 12 are sealed to each other about their peripheries and in between the thermoformed pockets 13 with seals 14. The seals 14 are hermetic seals 14. Pocket 13 defines an individual compartment for receiving a product 15, such as a capsule.

The first packaging component 11 includes a foil layer that is coated with an EVOH copolymer product-contacting sealant layer that has a higher ethylene content than the second packaging component 12. The second packaging component 12 includes multilayer thermoplastic film with a product-contacting sealant layer that has 38 mol percent or less of ethylene content. The multilayer thermoplastic film of the second packaging component 12 may include any number of film layers and film layer compositions depending upon both functional and aesthetic requirements of the blister component. It is desirable that multilayer thermoplastic film includes one or more film layers that are barrier materials and substantially chemically inert when in contact with a product. As it relates to the present disclosure, a barrier material can be provided by a single film layer or multiple film layers acting individually or in concert with each other, respectively. The phrase "substantially chemically inert" refers to materials that generally are not reactive with the product with which it comes into contact with and does not leech chemical ingredients into the product with which it comes into contact. Preferably, the second packaging component comprises a multilayer thermoplastic film which provides an average WVTR of 0.10 g/m² per 24 hours at 37.8 degrees Celsius, and 90 percent RH having a thickness of 381 microns (15 mil) before being thermoformed. The aforementioned features may be achieved by a multilayer thermoplastic film comprising at least 3 or 4 or 5 or 6 or 7 or 8 or 9 or 10 or 11 or 12 or 13 or more layers.

Tie layers, as generally known by a person having ordinary skill in the art, may be incorporated into the packaging components as appropriate.

Figure 4:
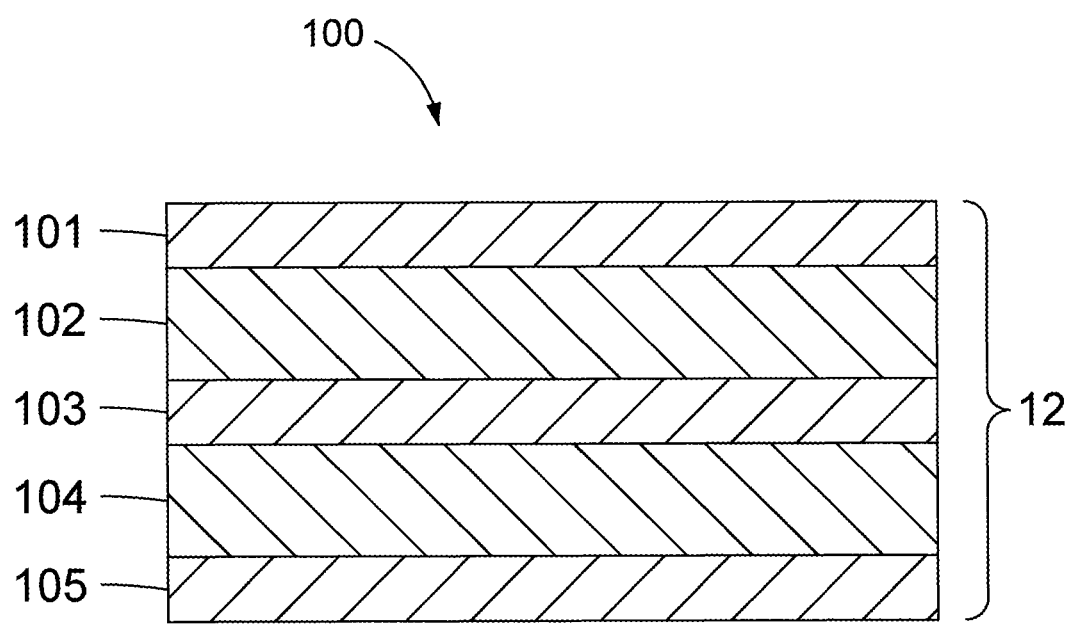
FIG. 4 illustrates a cross-section view of an embodiment of the second packaging component of the blister package shown in FIG. 1.

In one embodiment as depicted in FIG. 4, the second packaging component 12 comprises a multilayer thermoplastic film 100 comprising a five-layer structure of a first exterior layer 101 a first intermediate layer 102, a central core layer 103, a second intermediate layer 104, and a second exterior layer 105. In one embodiment, first and second exterior layers 101 and 105 comprise the same materials. In another embodiment, first and second exterior layers 101 and 105 comprise different materials.

Figure 5:
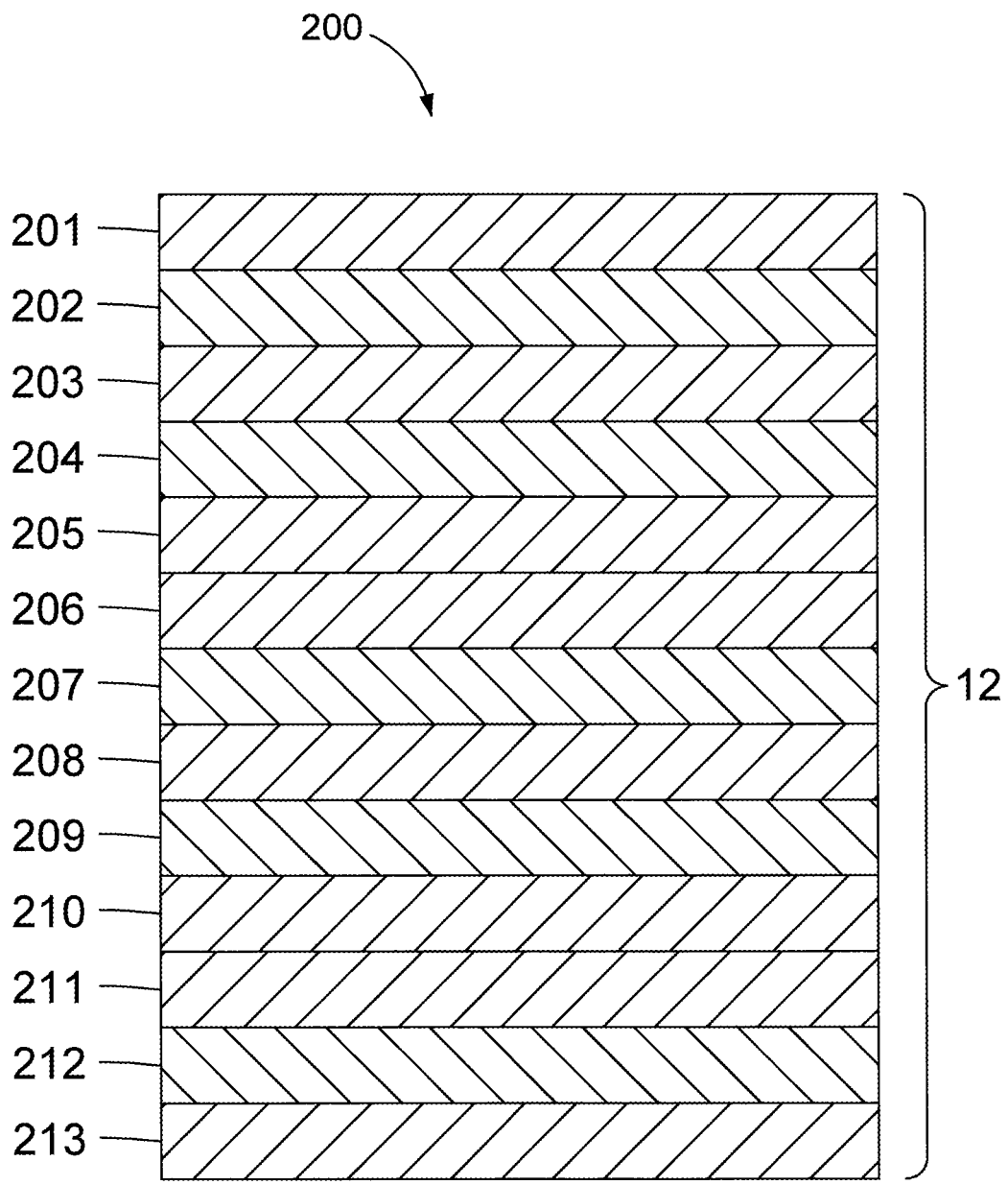
FIG. 5 illustrates a cross-section view of another embodiment of the second packaging component of the blister package shown in FIG. 1.

In another embodiment as depicted in FIG. 5, the second packaging component 12 comprises a multilayer palindromic thermoplastic film 200 which comprises a thirteen-layer symmetrical structure of a first exterior layer 201, a first intermediate layer 202, a second intermediate layer 203, a third intermediate layer 204, a fourth intermediate layer 205, a fifth intermediate layer 206, a central core layer 207, a sixth intermediate layer 208, a seventh intermediate layer 209, an eighth intermediate layer 210, a ninth intermediate layer 211, a tenth intermediate layer 212, and a second exterior layer 213. In this embodiment, film 200 comprises two exterior layers each comprising EVOH copolymer, two discrete intermediate layers each comprising EVOH copolymer, four discrete intermediate layers each comprising high density polyethylene (HDPE), and a layer of EVA. This thirteen-layer embodiment has the following layer sequence and general layer composition: EVOH/HDPE/tie/EVOH/tie/HDPE/EVA/HDPE/tie/EVOH/tie/HDPE/EVOH, wherein one of the exterior layers 201 or 213 comprises the second EVOH copolymer of the second packaging component 12. The tie layers are not shown in FIG. 4.

Figure 6:
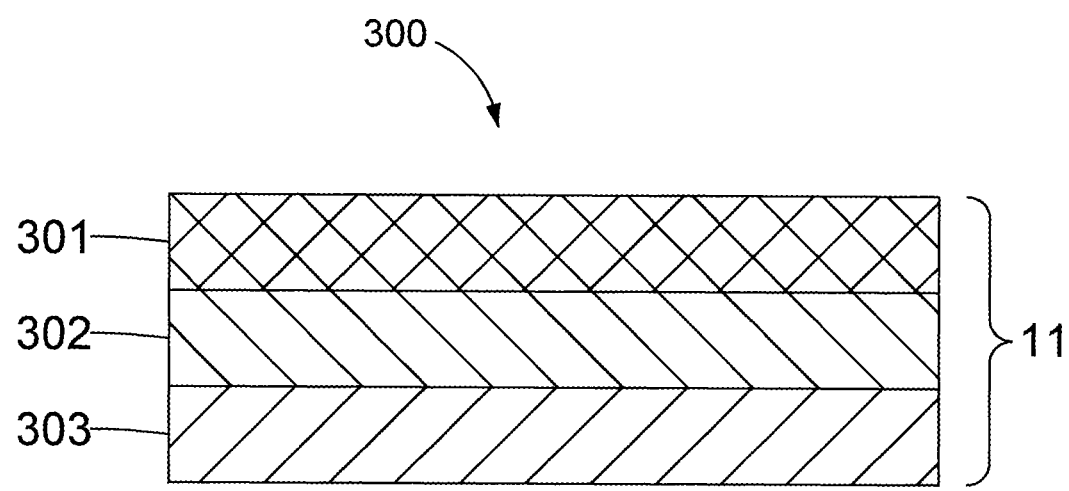
FIG. 6 illustrates a cross-section view of an embodiment of the first packaging component of the blister package shown in FIG. 1.

An embodiment of a first packaging component 11 is depicted in FIG. 6. In this embodiment, the first packaging component 11 comprises a laminate 300 having a first exterior layer 301, an intermediate layer 302 and a second exterior layer 303. The second exterior layer 303 comprises a first EVOH copolymer, first exterior layer 301 comprises a metal foil such as aluminum, and intermediate layer 302 comprises a tie or adhesive material bonding exterior layers 301 and 303 together.

Figure 7:
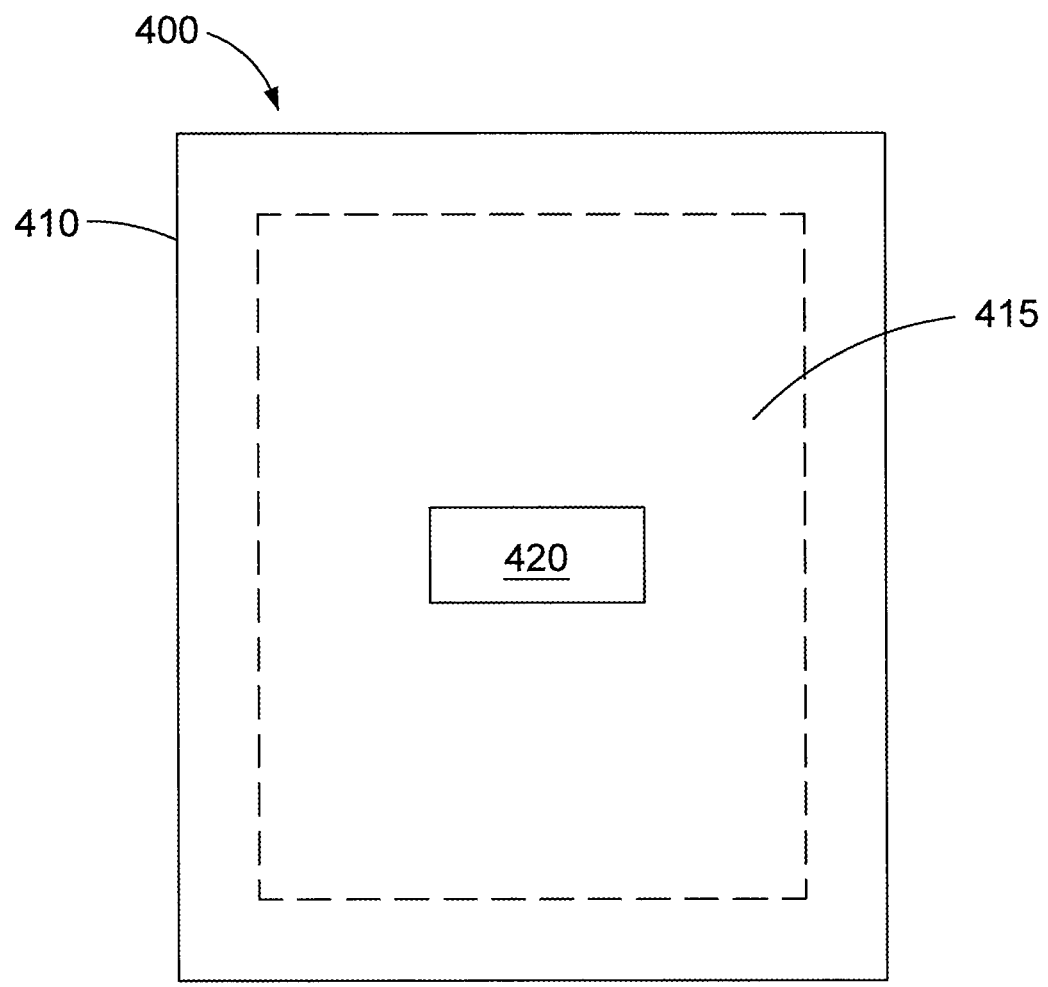
FIG. 7 illustrates a top view of another embodiment of a pouch package according to the present disclosure.

Referring now to FIG. 7, a package 400 is shown. The package 400 includes a product 420, such as a pharmaceutical product, sealed within an interior 415 of the package 400 that includes first packaging component 410 and a second packaging component (not shown). The product 420 is in contact with a product-contacting sealant layer of film 410. In some embodiments, two or more packaging components may be sealed together to form sealed interior 415, or the first packaging component 410 can be sealed to a container such that the first packaging component 410 and the container form the interior 415. In any embodiment, the first packaging component 410 forms at least a portion of the interior 415 of the package. In the depicted embodiment, the dashed lines indicate the sealed portion of the package 400 that defines sealed interior 415.

Unless defined otherwise, all technical and scientific terms used herein have the same meanings as commonly understood by one of ordinary skill in the art to which this invention belongs. All publications and patents specifically mentioned herein are incorporated by reference for all purposes.

The following examples are offered for illustrative purposes only and is not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Seal Strength.

Figure 8:
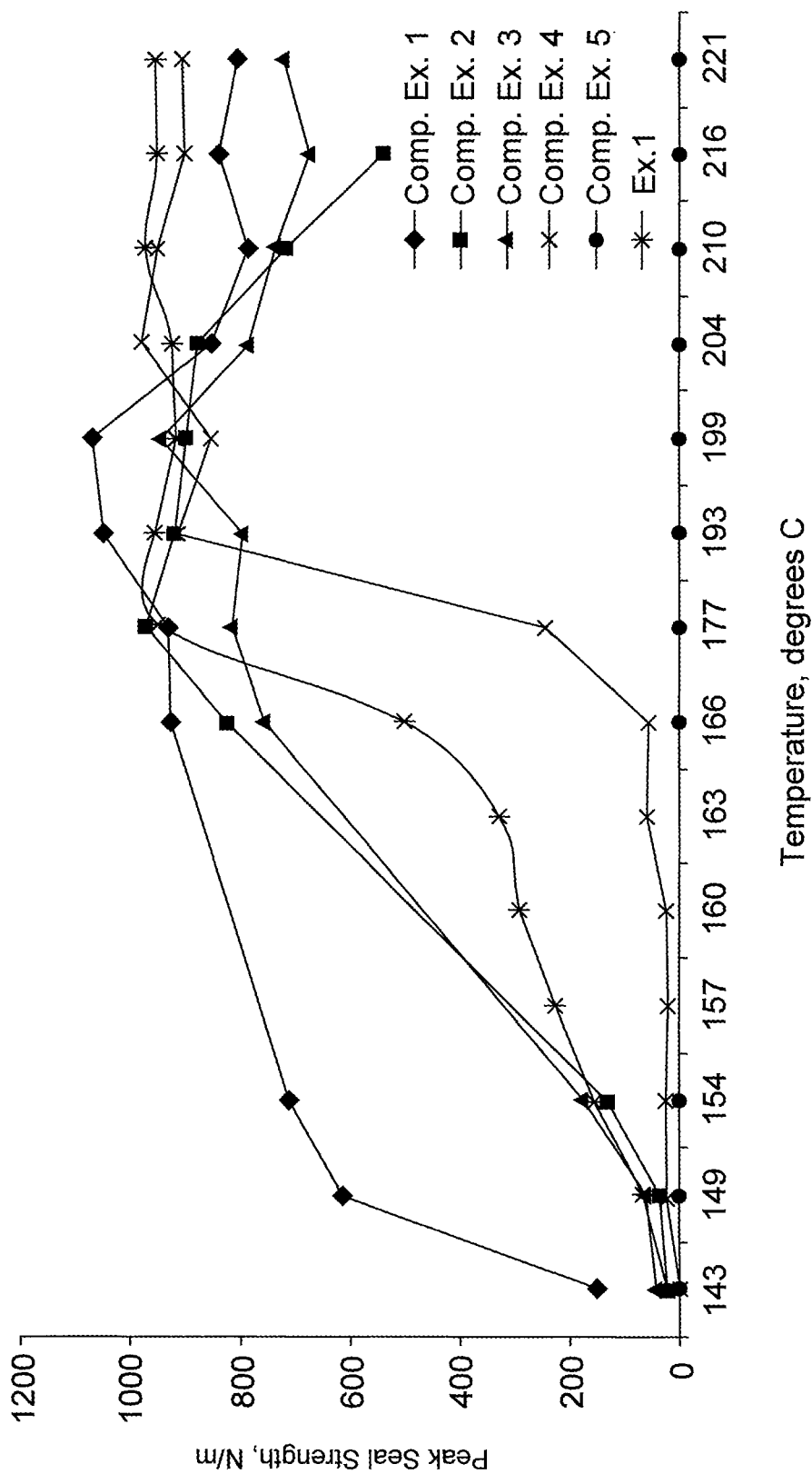
FIG. 8 illustrates a graphical representation of seal strength values of an embodiment of the present disclosure.

Packaging components listed in Table 5 were tested according to ASTM F88. A graphical representation of the seal strength results is shown in FIG. 8.

TABLE 5

| Code | First Packaging Component Structure | Second Packaging Component Structure |
| --- | --- | --- |
| Example 1 | Lid structure: Paper or OPET or similar/PE/foil/ with sealant layer of: 1) adhesive/LLDPE-LDPE with EVOH 48 mol percent ethylene; or 2)EAA-EVOH 48 mol percent coex or similar | Blister structure: EVOH 38 mol percent ethylene/tie/HDPE + nucleating agent + hydrocarbon resin/EVA//collapsed bubble |
| Comparative Example 1 | Film: 76.2 micron (3 mil) EVOH 48 mol percent ethylene | Film: 76.2 micron (3 mil) EVOH 48 mol percent ethylene |
| Comparative Example 2 | Film: 76.2 micron (3 mil) EVOH 38 mol percent ethylene | Film: 76.2 micron (3 mil) EVOH 38 mol percent ethylene |
| Comparative Example 3 | Film: 76.2 micron (3 mil) EVOH 48 mol percent ethylene | Film: 76.2 micron (3 mil) EVOH 38 mol percent ethylene |
| Comparative Example 4 | Lid structure: Paper or OPET or similar/PE/foil/ with sealant layer of: 1) adhesive/LLDPE-LDPE with EVOH 38 mol percent ethylene; or 2)EAA-EVOH 38 mol percent coex or similar | Blister structure: EVOH 38 mol percent ethylene/tie/HDPE + nucleating agent + hydrocarbon resin/EVA//collapsed bubble |
| Comparative Example 5 | Lid structure: Paper or OPET or similar/PE/foil/ COC 100 percent | Blister structure: EVOH 38 mol percent ethylene/tie/HDPE + nucleating agent + hydrocarbon resin/EVA//collapsed bubble |

Comparative Examples 1-3 include EVOH film bonded to another EVOH film. Example 1 and Comparative Examples 4 includes an EVOH lidding structure bonded to an EVOH blister structure. Comparative Examples 5 includes a non-EVOH lidding structure bonded to an EVOH blister structure. The effect of bonding thinner films to each other when compared to the effect of bonding relatively thicker blister package components can be seen among Example 1 and Comparative Examples 1-4, with thicker components displaying higher seal initiation temperatures. Comparative Example 4 demonstrates later seal initiation temperatures than Example 1. Comparative Example 5 is indicative of a package having a known anti-scalping lid and a known sealant for the blister that had surprisingly low seal strengths. Comparative Example 5 results indicate that the product-contacting layers should be somewhat similar, although do not need to be identical, in order to exhibit acceptable seal strengths.

Anti-Scalping/Migration

Figure 9:
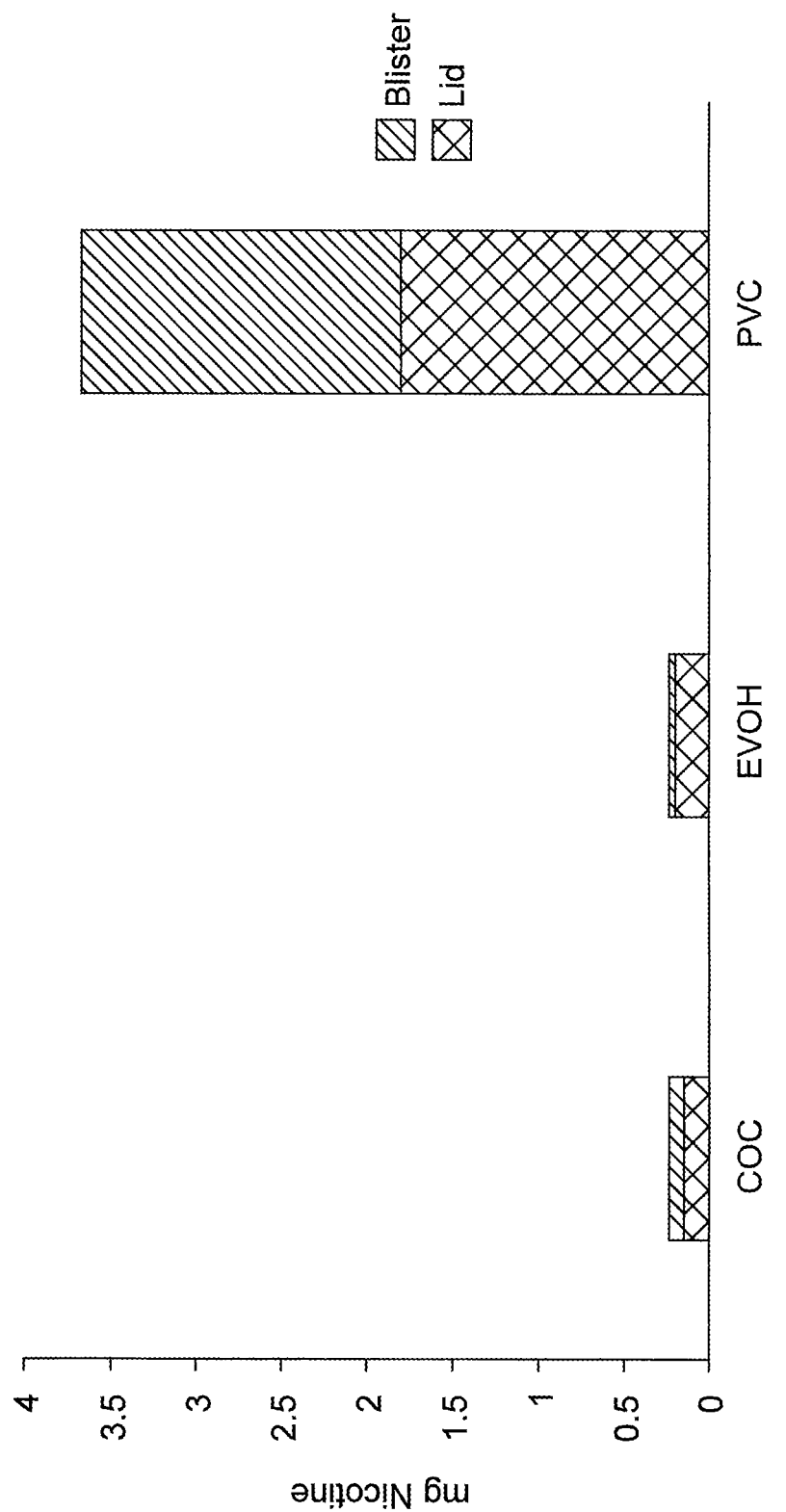
FIG. 9 illustrates a graphical representation of nicotine migration values of an embodiment of the present disclosure.

Blister packages with EVOH product-contacting layers of the present disclosure were tested to determine the degree of nicotine uptake. The first packaging component was in the form of a lid having a structure of outer layer/foil/EVOH 48 mol percent ethylene. The second packaging component was in the form of a blister having a structure of EVOH 38 mol percent ethylene/tie/HDPE+nucleating agent+hydrocarbon resin/EVA//collapsed bubble. Each of the EVOH product-contacting layers were 95 percent by weight EVOH. Comparative codes included the same lid structure as Example 1 except for the product-contacting sealant layer that included EVOH at different mol percent ethylene or COC as shown in Table 2. Comparative codes included the same blister structure as Example 1 except for the product-contacting sealant layer of EVOH that varied by mol percent ethylene as shown in Table 2. The same amount of nicotine was placed into each blister package. The packages were aged for 4 weeks under controlled conditions of 38 degrees Celsius (100 degrees Fahrenheit) and relative humidity of 20 percent. The amount of nicotine uptake in the blister package materials, after washing out the nicotine from the blister package, was measured after 2 weeks and 4 weeks of elapsed time. Table 3 includes the nicotine migration data at 2 weeks. Week 4 results indicated that the nicotine that was extracted was much lower than at week 2. Yellowing and browning of the week 4 samples indicated that the nicotine degraded (oxidized) and could not quantified as nicotine. A graphical representation of the data in Table 6 is shown in FIG. 9.

TABLE 6

| Blister Package | Week 2 Nicotine Migration (mg) | | |
|---|---|---|---|
| | Lid | Blister | Total |
| EVOH: Lid- 48 mol percent; Blister - 38 mol percent | 0.184 | 0.008 | 0.192 |
| CXB: Lid-COC; Blister-COC (commercially available CXB sealant layer on SKYBLUE blister packaging film with the product-contacting layers including 100 wt. percent COC) | 0.147 | 0.07 | 0.217 |
| PVC: Lid-foil with vinyl acrylic heat seal coating; Blister-monolayer PVC (commercially available standard blister packaging) | 1.865 | 1.86 | 3.725 |

Embodiments

Embodiment A: A package comprising
a. a first packaging component comprising a product-contacting sealant layer comprising a first ethylene vinyl alcohol copolymer; and
b. a second packaging component comprising a product-contacting sealant layer comprising a second ethylene vinyl alcohol copolymer;
wherein the ethylene content of the second ethylene vinyl alcohol copolymer is equal to or less than 38 percent, and wherein the ethylene content of the first ethylene vinyl alcohol copolymer is greater than the ethylene content of the second ethylene vinyl alcohol copolymer.

Embodiment B: A package according to Embodiment A, wherein the ethylene content of the second ethylene vinyl alcohol copolymer is 38 percent.

Embodiment C: A package according to Embodiment A or B, wherein the ethylene content of the first ethylene vinyl alcohol copolymer is greater than 38 percent.

Embodiment D: A package according to any one of Embodiments A-C, wherein the first packaging component comprises at least 95 wt. percent of the first ethylene vinyl alcohol copolymer and the second packaging component comprises at least 95 wt. percent of the second ethylene vinyl alcohol copolymer.

Embodiment E: A package according to any one of Embodiments A-D, wherein the first packaging component consists essentially of the first ethylene vinyl alcohol copolymer and the second packaging component consists essentially of the second ethylene vinyl alcohol copolymer.

Embodiment F: A package according to any one of Embodiments A-E, wherein the first and second ethylene vinyl alcohol copolymers are heat sealed to each other under conditions of 163 degrees Celsius to 193 degrees Celsius, 1 second dwell time and 0.2 MPa pressure and comprise a peak heat seal strength of at least 525 Newton/m (3 pounds-force/inch) when tested according to ASTM F88.

Embodiment G: A package according to any one of Embodiments A-F, further comprising a water or moisture transmission rate (WVTR) 0.1 $g/m^2/24$ hours at 38 degrees Celsius and 90 percent relative humidity according to ASTM F1249.

Embodiment H: A package according to any one of Embodiments A-G, further comprising an oxygen transmission rate (OTR) of equal to or less than 0.25 $cc/m^2/24$ hours at 1 atmosphere and 23 degrees Celsius and 0 percent relative humidity according to ASTM F1927.

Embodiment I: A package according to any one of Embodiments A-H, wherein the package is in the form of a pouch, sachet, or thermoformed blister and/or tray and lid.

Embodiment J: A package according to any one of Embodiments A-I, further comprising a pharmaceutical active agent that is hermetically sealed within the package, wherein the pharmaceutical active agent is selected from the group consisting of nicotine, tetrahydrocannabinol (THC), fentanyl, acetylfentanyl, lidocaine, clonidine, ethinyl estradiol, estradiol, oxybutynin, buprenorphine, granisetron, methylphenidate, and scopolamine.

Embodiment K: A package according to any one of Embodiments A-J, further comprising a RED value of 1.0 or greater.

Embodiment L: A package comprising:
a. a first packaging component comprising a first ethylene vinyl alcohol copolymer; and
b. a second packaging component comprising a second ethylene vinyl alcohol copolymer;
wherein the first ethylene vinyl alcohol copolymer has an ethylene content of about 48 mol percent, wherein the second ethylene vinyl alcohol copolymer has an ethylene content of about 38 mol percent, and wherein the first and second ethylene vinyl alcohol copolymers are heat sealed to each other.

Embodiment M: The package according to Embodiment L, wherein the first packaging component is a flexible film and the second packaging component is a formable film.

Embodiment N: The packaged product according to any one of Embodiments L-M, wherein the pharmaceutical active agent comprises nicotine, tetrahydrocannabinol (THC), acetylfentanyl, lidocaine, or a combination thereof.

Embodiment O: A package comprising:
a. a first packaging component comprising a product-contacting sealant layer comprising a first ethylene vinyl alcohol copolymer and an aluminum foil layer: and
b. a second packaging component comprising a product-contacting sealant layer comprising a second ethylene vinyl alcohol copolymer and a barrier layer comprising ethylene vinyl acetate (EVA);

wherein the first ethylene vinyl alcohol copolymer has an ethylene content of 48 mol percent, wherein the second ethylene vinyl alcohol copolymer has an ethylene content of 38 mol percent, and wherein the first and second ethylene vinyl alcohol copolymers are heat sealed to each other.

Embodiment P: A packaged product comprising the package according to any previous Embodiment, wherein the product is located between the first packaging component and the second packaging component, and wherein the product comprises a pharmaceutical active agent.

What is claimed is:

1. A package comprising:
    a first packaging component comprising a product-contacting sealant layer comprising a first ethylene vinyl alcohol copolymer; and
    a second packaging component comprising a product-contacting sealant layer comprising a second ethylene vinyl alcohol copolymer;
  wherein the ethylene content of the second ethylene vinyl alcohol copolymer is equal to or less than 38 percent, and wherein the ethylene content of the first ethylene vinyl alcohol copolymer is greater than the ethylene content of the second ethylene vinyl alcohol copolymer, wherein the product-contacting sealant layer of the first packaging component is an interior surface layer, and wherein the product-contacting sealant layer of the second packaging component is an interior surface layer.

2. A package according to claim 1, wherein the ethylene content of the second ethylene vinyl alcohol copolymer is 38 percent.

3. A package according to claim 2, wherein the ethylene content of the first ethylene vinyl alcohol copolymer is greater than 38 percent.

4. A package according to claim 1, wherein the first packaging component comprises at least 95 wt. percent of the first ethylene vinyl alcohol copolymer and the second packaging component comprises at least 95 wt. percent of the second ethylene vinyl alcohol copolymer.

5. A package according to claim 1, wherein the first packaging component consists essentially of the first ethylene vinyl alcohol copolymer and the second packaging component consists essentially of the second ethylene vinyl alcohol copolymer.

6. A package according to claim 1, wherein the first and second ethylene vinyl alcohol copolymers are heat sealed to each other under conditions of 163 degrees Celsius to 193 degrees Celsius, 1 second dwell time and 0.2 MPa pressure and comprise a peak heat seal strength of at least 525 Newton/m (3 pounds-force/inch) when tested according to ASTM F88.

7. A package according to claim 1, further comprising a water or moisture transmission rate (WVTR) 0.1 $g/m^2/24$ hours at 38 degrees Celsius and 90 percent relative humidity according to ASTM F1249.

8. A package according to claim 1, further comprising an oxygen transmission rate (OTR) of equal to or less than 0.25 $cc/m^2/24$ hours at 1 atmosphere and 23 degrees Celsius and 0 percent relative humidity according to ASTM F1927.

9. A package according to claim 1, wherein the package is in the form of a pouch, sachet, or thermoformed blister and/or tray and lid.

10. A package according to claim 1, further comprising a pharmaceutical active agent that is hermetically sealed within the package, wherein the pharmaceutical active agent is selected from the group consisting of nicotine, tetrahydrocannabinol (THC), fentanyl, acetylfentanyl, lidocaine, clonidine, ethinyl estradiol, estradiol, oxybutynin, buprenorphine, granisetron, methylphenidate, and scopolamine.

11. A package according to claim 1, further comprising a RED value of 1.0 or greater.

12. A packaged product comprising the package according to claim 1, wherein a product is located between the first packaging component and the second packaging component, and wherein the product comprises a pharmaceutical active agent.

13. The packaged product according to claim 12, wherein the pharmaceutical active agent comprises nicotine, tetrahydrocannabinol (THC), acetylfentanyl, lidocaine, or a combination thereof.

14. A package comprising:
    a first packaging component comprising a product-contacting sealant layer comprising a first ethylene vinyl alcohol copolymer and an aluminum foil layer; and
    a second packaging component comprising a product-contacting sealant layer comprising a second ethylene vinyl alcohol copolymer and a barrier layer comprising ethylene vinyl acetate (EVA);
  wherein the first ethylene vinyl alcohol copolymer has an ethylene content of 48 mol percent, wherein the second ethylene vinyl alcohol copolymer has an ethylene content of 38 mol percent, and wherein the first and second ethylene vinyl alcohol copolymers are heat sealed to each other, wherein the product-contacting sealant layer of the first packaging component is an interior surface layer, and wherein the product-contacting sealant layer of the second packaging component is an interior surface layer.

15. A package according to claim 2, wherein the first packaging component comprises at least 95 wt. percent of the first ethylene vinyl alcohol copolymer and the second packaging component comprises at least 95 wt. percent of the second ethylene vinyl alcohol copolymer.

16. A package according to claim 3, wherein the first packaging component comprises at least 95 wt. percent of the first ethylene vinyl alcohol copolymer and the second packaging component comprises at least 95 wt. percent of the second ethylene vinyl alcohol copolymer.

17. A package according to claim 2, wherein the first packaging component consists essentially of the first ethylene vinyl alcohol copolymer and the second packaging component consists essentially of the second ethylene vinyl alcohol copolymer.

18. A package according to claim 3, wherein the first packaging component consists essentially of the first ethylene vinyl alcohol copolymer and the second packaging component consists essentially of the second ethylene vinyl alcohol copolymer.

* * * * *

UNITED STATES PATENT AND TRADEMARK OFFICE
CERTIFICATE OF CORRECTION

PATENT NO. : 11,939,132 B2
APPLICATION NO. : 17/295784
DATED : March 26, 2024
INVENTOR(S) : Michael D. Priscal and Kevin P. Nelson It is certified that error appears in the above-identified patent and that said Letters Patent is hereby corrected as shown below:

In the Specification

Column 4, Line 45 Delete "carder" and insert -- carrier --, therefor.

Column 11, Line 20 Delete "polylactic acid" and insert -- poly(lactic acid) --, therefor.

Column 11, Line 30 Delete "polyimide" and insert -- polyamide --, therefor.

Column 13, Line 30 Delete "quinaridones" and insert -- quinacridones --, therefor.

Column 18, Line 18 Delete "granisitron" and insert -- granisetron --, therefor.

Column 19, Line 30 Delete "produce" and insert -- product --, therefor.

Signed and Sealed this
Twenty-ninth Day of April, 2025

Coke Morgan Stewart
*Acting Director of the United States Patent and Trademark Office*